(12) United States Patent
Drexl et al.

(10) Patent No.: US 12,096,992 B2
(45) Date of Patent: Sep. 24, 2024

(54) METHOD OF CALIBRATING A MEDICAL INSTRUMENT USING VIRTUAL MODELS

(71) Applicant: Brainlab AG, Munich (DE)

(72) Inventors: Thomas Drexl, Munich (DE); Melanie Wegner, Munich (DE)

(73) Assignee: Brainlab AG, Munich (DE)

( * ) Notice: Subject to any disclaimer, the term of this patent is extended or adjusted under 35 U.S.C. 154(b) by 1008 days.

(21) Appl. No.: 17/049,634

(22) PCT Filed: Mar. 16, 2020

(86) PCT No.: PCT/EP2020/057128
§ 371 (c)(1),
(2) Date: Oct. 22, 2020

(87) PCT Pub. No.: WO2020/193256
PCT Pub. Date: Oct. 1, 2020

(65) Prior Publication Data
US 2021/0236208 A1    Aug. 5, 2021

(30) Foreign Application Priority Data

Mar. 22, 2019   (WO) ................ PCT/EP2019/057310

(51) Int. Cl.
*A61B 34/20*   (2016.01)
*A61B 34/10*   (2016.01)
(Continued)

(52) U.S. Cl.
CPC .... *A61B 34/20* (2016.02); *A61B 2017/00725* (2013.01); *A61B 2034/102* (2016.02);
(Continued)

(58) Field of Classification Search
None
See application file for complete search history.

(56) References Cited

U.S. PATENT DOCUMENTS 6,351,659 B1   2/2002 Vilsmeier
6,996,487 B2   2/2006 Jutras et al.
(Continued)

FOREIGN PATENT DOCUMENTS

WO   WO-2006067371 A1 *  6/2006 ........... A61B 5/0002
WO   2015117644 A1       8/2015

OTHER PUBLICATIONS

International Search Report and Written Opinion for corresponding International Application No. PCT/EP2020/057128, dated Jun. 12, 2020. 14 Pages.
(Continued)

*Primary Examiner* — Tahmina N Ansari
(74) *Attorney, Agent, or Firm* — Tucker Ellis LLP

(57) ABSTRACT

A computer implemented medical method of calibrating a medical instrument is provided. The method calculates a position of the instrument tip model within the indentation model, associated with an estimated position of the instrument tip within the indentation and calibrates the medical instrument, thereby using the determined position of the instrument tip model. The position of any arbitrary medical instrument tip, such as an indentation of a calibration device, can be estimated. This is an improvement of accuracy in view of the generic approach of using the same reference point of the indentation of the calibration device for any arbitrary medical instrument tip. A virtual model of a shape of a medical instrument, such as the instrument tip, is matched onto a virtual model of a shape of a calibration device, such as an indentation of the calibration device.

20 Claims, 7 Drawing Sheets

(51) Int. Cl.
*A61B 90/00* (2016.01)
*A61B 17/00* (2006.01)

(52) U.S. Cl.
CPC ............ *A61B 2034/2055* (2016.02); *A61B 2034/2068* (2016.02); *A61B 2090/3945* (2016.02)

(56) References Cited

U.S. PATENT DOCUMENTS

| | | | |
|---|---|---|---|
| 7,166,114 B2 | 1/2007 | Moctezuma De La Barrera | |
| 10,499,996 B2* | 12/2019 | de Almeida Barreto | ................... G06T 19/006 |
| 2006/0260147 A1 | 11/2006 | Pelletier | |
| 2010/0295931 A1* | 11/2010 | Schmidt | ................ A61B 34/20 345/633 |
| 2011/0319912 A1 | 12/2011 | Nishio | |
| 2018/0071032 A1* | 3/2018 | de Almeida Barreto | ................... G06T 19/006 |
| 2018/0132946 A1* | 5/2018 | Kao | ................... G06T 7/248 |
| 2021/0236208 A1* | 8/2021 | Drexl | ................... A61B 34/20 |

OTHER PUBLICATIONS

Kirill Koulechov, "Leistungssteuerung chirurgischer Instrumente in der Kopf-Chirurgie", Technical University of Munich, Munich, Germany Apr. 26, 2006 (Apr. 26, 2006), Retrieved from the Internet: URL:https://mediatum.ub.tum.de/doc/601976/601976.pdf; Sep. 6, 2019.

Timo Krüger, "Ein modulares Navigationssystem für die dentale Implantologie",Nov. 16, 2006 (Nov. 16, 2006), p. 83, URL:https://epo.summon.serialssolutions.com/2.0.0/link/0/eLvHCXMwrV1LSwMxEB66CKInX-ATcvC6Ntud3XQLKIL6ENSD9OJpSTIT6MG2aPHXefOPmewDe_Og-QEZJsnkg5lvvgG49MEnGTOMXWFUjFiksUaJsSY0LpNMru qveBnibKKeJ_jQAdv2wgRaZZgbpX3AX3GrJdRd_eSwbpsjvafrJZ X18o9sMLC9xLHSKjceZK2T7KxMbdF3qTFJZiiCylNhU9nEniq6 xBUzKvQHxkk9ar61vQEy4z3.

* cited by examiner

US 12,096,992 B2

METHOD OF CALIBRATING A MEDICAL INSTRUMENT USING VIRTUAL MODELS

RELATED APPLICATION DATA

This application is a national phase application of International Application No. PCT/EP2020/057128 filed Mar. 16, 2020, which claims priority to International Application No. PCT/EP2019/057310, filed on Mar. 22, 2019, the contents of which are incorporated herein by reference.

FIELD OF THE INVENTION

The present invention relates to a computer-implemented medical method of calibrating a medical instrument, a use of the estimated position of the instrument tip, an instrument calibration system, a surgical navigation system for computer assisted surgery as well as a computer program.

TECHNICAL BACKGROUND

Calibration of surgical instruments is commonly carried out by holding an instrument onto a calibration device. This features a calibration workflow to calibrate and verify surgical instruments. The instrument tip, which is typically the foremost point of the instrument, is held into a fitting hole or into indentations or protrusions so the tip position is fixed even while the instrument handle, where the user holds the instrument, is moving.

Additionally, a tracking system identifies markers, for example infrared-reflecting spheres, attached to the calibration device and the instrument, and provides coordinates in the tracking system's own coordinate system, thus the spatial relationship between instrument and calibration device is determined.

The navigation system then calculates the instrument tip position from knowing the calibration device's reference point, where the instrument tip is in a fixed position, by selecting or automatically detecting it from special instrument movements like a movement of the handle or like the rotation of the instrument around its longitudinal axis.

When the instrument tip is being held into the indentation of the calibration device, a position of the instrument in the indentation normally is determined by assuming that the instrument tip is located at the deepest point of the indentation, the so called pivot point. Using this pivot point, the instrument is calibrated for the tracking system.

However, there are many instruments and tip shapes that do not fit in any of the provided shapes/indentations on common calibration devices, so unwanted systematic error is introduced. Assembling a calibration device that allows to calibrate all possible tips shapes has been declined due to many reasons, in particular usability and expenses. In addition, the tip of the instrument, which normally is distant to the markers of the instrument, needs to be calibrated in order to prevent systematic error of a deformed instrument. Such deformation might be introduced by bending the instrument when using it, or by manufacturing errors. Furthermore, systematic error is added from the tracking system, in particular from passive markers.

The present invention can be used for calibration procedures e.g. in connection with a system for image-guided surgery such as in Spine & Trauma navigation.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the light of the prior art descripted hereinbefore, it is the main object of the present invention to provide an improved method for calibrating a medical instrument, in particular in view of a deviation between the position of the instrument tip and the position of the pivot point of the indentation of the calibration device, when the instrument tip is held within the indentation during calibration.

In the following, a short description of the specific features of the present invention is given which shall not be understood to limit the invention only to the features or a combination of the features described in this section.

A computer implemented medical method of calibrating a medical instrument is presented.

In particular, this method determines a position of an instrument model of a medical instrument within an indentation model of an indentation of a calibration device. This position is represented by an updated reference point and associates with an estimation of the position of the instrument tip in the indentation of the calibration device in the real world. This updated reference point deviates from a reference point defined by the deepest point of the indentation of the calibration device, where the instrument tip would be ideally located when holding the instrument tip into the indentation. One technical effect of the invention is that the position of any arbitrary medical instrument tip, in particular in an indentation of a calibration device, can be estimated. This is an improvement of accuracy in view of the generic approach of using the same reference point of the indentation of the calibration device for any arbitrary medical instrument tip. In other words, the accuracy of the calibration of the instrument can be improved, as instead of assuming that the instrument tip is exactly located at the deepest point of the indentation of the calibration device, a real position of the instrument tip in the indentation is estimated based on matching an instrument tip model onto an indentation model.

GENERAL DESCRIPTION OF THE INVENTION

In this section, a description of the general features of the present invention is given for example by referring to possible embodiments of the invention.

This is achieved by the subject-matter of the independent claims, wherein further embodiments are incorporated in the dependent claims and the following description.

The described embodiments similarly pertain to the computer-implemented medical method of calibrating an instrument, the use of the estimated position of the instrument tip, the instrument calibration system, the surgical navigation system for computer assisted surgery and the computer program. Synergetic effects may arise from different combinations of the embodiments although they might not be described in detail hereinafter. Furthermore, it shall be noted that all embodiments of the present invention concerning a method, might be carried out with the order of the steps as explicitly described herein. Nevertheless, this has not to be the only and essential order of the steps of the method. The herein presented methods can be carried out with another order of the disclosed steps without departing from the respective method embodiment, unless explicitly mentioned to the contrary hereinafter.

Technical terms are used by their common sense. If a specific meaning is conveyed to certain terms, definitions of terms will be given in the following in the context of which the terms are used.

According to the present disclosure, a computer implemented medical method of calibrating a medical instrument is provided. The method comprises the steps providing an instrument model comprising an instrument tip model, wherein the instrument tip model is a virtual model of a shape of the medical instrument comprising an instrument tip. Furthermore, providing a calibration device model comprising an indentation model, wherein the indentation model is virtual model of a shape of a calibration device comprising an indentation onto which the instrument tip is introduced for calibration. Further, matching the instrument tip model onto the indentation model, thereby determining a position of the instrument tip model within the indentation model. Additionally, calibrating the medical instrument, thereby using the determined position of the instrument tip model.

The determined position of the instrument tip model within the indentation model is associated with an estimated position of the instrument tip within the indentation. In other words the determined position of the instrument tip model within the indentation model defines a spatial relationship between the instrument tip model and the indentation model. Consequently, this spatial relationship can be assumed for the instrument tip and the indentation in the real world leading to an estimated position of the instrument tip within the indentation.

The medical instrument comprises at least a handle portion for holding the instrument and an instrument tip that is used for the medical procedure. Thus, the medical instrument model, being a virtual model of a shape of the instrument, also comprises an instrument tip model. In other words, the instrument tip model is preferably part of the instrument model. Accordingly, the indentation model is preferably part of the calibration device model.

The deepest point of the indentation of the calibration device, which is also called pivot point, is considered the reference point for calibration, wherein the reference point marks the expected ideal position of the medical instrument tip in the indentation, when holding the instrument into the indentation for calibration of the instrument. However, the instrument tip in reality might not be located directly at this reference point. Thus, during calibration of the instrument, a systematic error is introduced. By determining a position of the instrument model in relation to the indentation model, an estimated position of the instrument tip in the indentation is determined. In other words, the estimated position of the instrument tip is marked by a new or updated reference point, compared to the original reference point determined by the pivot point of the indentation.

The method presented herein is directed to the calculation of a new or updated reference point for a surgical navigation system, which deviates from the reference point of the calibration device. This new reference point is the determined position of the instrument tip model within the indentation model, as calculated by the method of the present invention, relating to an estimated position of the instrument tip within the indentation.

The updated reference point preferably is defined by the point of the instrument tip that is expected to be used as reference for the indentation. In general, the instrument tip is defined by an end point of the instrument along the longitudinal axis of the instrument. The point of the instrument tip is considered for the updated reference point and thus an origin of an instrument tip coordinate system is preferably predefined in this point of the instrument tip of the instrument model. For example, at an instrument tip with a flat triangular end, the updated reference point is defined at the centre of the triangle at the bottom of the instrument.

Thus, a position of an instrument tip can be estimated for any arbitrary instrument tip. The term "arbitrary", as used herein, relates to the fact that the position of any shape of instrument tip can be estimated in the indentation. However, the shape of the arbitrary instrument tip is preferably already known and the instrument tip model is available.

The term "matching onto", as used herein, comprises finding collision points between the instrument tip model and the calibration device model relating to a possible position of the instrument tip.

In a preferred embodiment, the instrument model and/or the calibration device model are 3D models.

The calibration device can be formed as a separate device. However, preferably, the calibration device is integrated in an already existing device, like for example an instrument itself. Generally, any trackable device comprising a suitable indentation can be used for calibration.

In a preferred embodiment, a patient reference array attached to the patient comprises the indentation onto which the instrument tip is introduced for calibration.

The indentation preferably is cone shaped. However, other shapes are possible as well. In view of the variety of different shapes of available instrument tips, an indentation with a constant gradient is preferred.

The term "instrument model" and/or "calibration device model" preferably relate to the instrument and/or calibration device, respectively. It is therefore clear that in the computer implemented medical method models of the instrument and/or the calibration are used relating to the instrument and/or the calibration device, respectively.

In the following definitions for the terms used in in the context of the first aspect of the present invention are provided.

Computer Implemented Method

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Marker

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

Marker Device

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows determining the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

Marker Holder

A marker holder is understood to mean an attaching device for an individual marker which serves to attach the marker to an instrument, a part of the body and/or a holding element of a reference star, wherein it can be attached such that it is stationary and advantageously such that it can be detached. A marker holder can for example be rod-shaped and/or cylindrical. A fastening device (such as for instance a latching mechanism) for the marker device can be provided at the end of the marker holder facing the marker and assists in placing the marker device on the marker holder in a force fit and/or positive fit.

Pointer

A pointer is a rod which comprises one or more—advantageously, three—markers fastened to it and which can be used to measure off individual co-ordinates, for example spatial co-ordinates (i.e. three-dimensional co-ordinates), on a part of the body, wherein a user guides the pointer (for example, a part of the pointer which has a defined and advantageously fixed position with respect to the at least one marker attached to the pointer) to the position corresponding to the co-ordinates, such that the position of the pointer can be determined by using a surgical navigation system to detect the marker on the pointer. The relative location between the markers of the pointer and the part of the pointer used to measure off co-ordinates (for example, the tip of the pointer) is for example known. The surgical navigation system then enables the location (of the three-dimensional co-ordinates) to be assigned to a predetermined body structure, wherein the assignment can be made automatically or by user intervention.

Reference Star

A "reference star" refers to a device with a number of markers, advantageously three markers, attached to it, wherein the markers are (for example detachably) attached to the reference star such that they are stationary, thus providing a known (and advantageously fixed) position of the markers relative to each other. The position of the markers relative to each other can be individually different for each reference star used within the framework of a surgical navigation method, in order to enable a surgical navigation system to identify the corresponding reference star on the basis of the position of its markers relative to each other. It is therefore also then possible for the objects (for example, instruments and/or parts of a body) to which the reference star is attached to be identified and/or differentiated accordingly. In a surgical navigation method, the reference star serves to attach a plurality of markers to an object (for example, a bone or a medical instrument) in order to be able to detect the position of the object (i.e. its spatial location and/or alignment). Such a reference star for example features a way of being attached to the object (for example, a clamp and/or a thread) and/or a holding element which ensures a distance between the markers and the object (for example in order to assist the visibility of the markers to a marker detection device) and/or marker holders which are mechanically connected to the holding element and which the markers can be attached to.

Navigation System

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

The invention also relates to a navigation system for computer-assisted surgery, comprising:
- a computer for processing the absolute point data and the relative point data;
- a detection device for detecting the position of the main and auxiliary points in order to generate the absolute point data and to supply the absolute point data to the computer;
- a data interface for receiving the relative point data and for supplying the relative point data to the computer; and
- a user interface for receiving data from the computer in order to provide information to the user, wherein the received data are generated by the computer on the basis of the results of the processing performed by the computer.

Surgical Navigation System

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

Referencing

Determining the position is referred to as referencing if it implies informing a navigation system of said position in a reference system of the navigation system.

For example, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity.

In the following preferred embodiments will be described in more detail.

Preferably, the method comprises the step of using the determined position of the instrument tip model, relating to the estimated position of the instrument tip, as an updated reference point in a surgical navigation system.

Thus, the estimated position of the instrument tip is more accurate than the generic reference point of a calibration device for a surgical navigation system, in particular of an indentation of the calibration device. Therefore, the accuracy of a calibration of the instrument tip with the calibration device is improved.

According to another exemplary embodiment of the present invention, the method comprises the step of tracking the instrument by a tracking device and a, preferably passive, tracker arranged on the instrument.

The step of tracking is preferably carried out during the matching process, which results in the estimated position of the instrument tip.

Thus, using the determined position of the instrument tip model, the calibration and the tracking of the instrument can be improved.

According to another exemplary embodiment of the present invention, matching the instrument tip model onto the indentation model comprises determining an instrument model coordinate system, InstModel, and calibrating the medical instrument, thereby using the determined instrument model coordinate system, InstModel.

In other words, matching the instrument tip model onto the indentation model comprises determining an instrument model coordinate system in relation to the indentation model, thereby using the determined position of the instrument tip model within the indentation model and calibrating the medical instrument, thereby using the determined instrument model coordinate system in relation to the indentation model.

The term "coordinate system", as used herein, describes a position and orientation of an object in a predetermined space. Preferably, in a tracking system, every marker array defines its own coordinate system. In other words, the marker array in particular defines origin and directions of the coordinate system, from which positions of objects can be described. During tracking, a tracking system identifies the different marker arrays and thus coordinate systems and sets them in a relationship to each other. Thus, a position of each marker array in relation to the tracking system is determined.

The term "transformation", as used herein, specifically describes a translation and/or rotation between two objects like tracking system and calibration device. As each object is represented by a location and orientation in space, preferably a coordinate system is defined for each object, so the transformation allows to describe coordinates of points in one system in terms of coordinates in another system. For example, the pivot point of the calibration device is given in local coordinates of the calibration device. Using the transformation from calibration device to instrument tip, the pivot point can be represented in instrument tip coordinates. Every transformation has a unique reverse transformation, so the tip in instrument tip coordinates can also be represented in calibration device coordinates. To optimize the meaning of coordinate systems, their origin is typically located at a point of interest within their object. Thus the instrument tip coordinate system origin is defined at the tip of the instrument. A preferable implementation of such transformations is the usage of projective 4×4 matrices that are widely used in the field of computer graphics for exactly this purpose. Thus one transformation matrix can include translation and rotation, theoretically every affine transformation in 3D space, and it leaves the matrix invertible. A composition of transformations like calibration device to camera, then camera to instrument marker array is represented by a multiplication of the according matrices (in reverse order). A transformation between two coordinate systems can be set up by knowing the origin and three perpendicular axes of one coordinate system in the coordinates of the other coordinate system. For 4×4 matrices the commonly used technique is a change of basis where the axes are normalized and written into the upper 3×3 part of the 4×4 matrix while the translation between the coordinate systems is taken into account in the $4^{th}$ column.

In a tracking setup for a calibration of the instrument, different coordinate systems of the participating objects of the tracking system need to be related to each other. In other words, the tracking system, in particular the camera, comprises a camera coordinate system, the calibration device comprises a calibration device coordinate system, and the instrument comprises an instrument marker coordinate system at its marker array and an instrument tip coordinate system at its tip.

For calibrating the instrument, it is necessary to find a relationship between the instrument tip and the calibration device. By holding the instrument tip of the instrument into the indentation of the calibration device, this relationship can be determined since it is assumed that the translation between the calibration device and the instrument tip is known.

The orientation of the instrument tip coordinate system is preferable pre-defined in relation to the instrument marker coordinate system. However, planes or other features of the calibration device can be used to specifically calibrate the axis of an instrument, which is not the main object of this invention.

With the help of an instrument model, including an instrument tip model, and a calibration device model, including an indentation model, the position of the instrument tip model within the indentation model is determined for a situation in which the instrument is held into the indentation of the calibration device for calibration of the instrument. So far, when holding the instrument into the indentation of the calibration device, the position of the instrument tip is assumed at the pivot point of the indentation. Consequently, this point is used as origin for an instrument tip coordinate system used for calibration of the instrument. Instead of assuming the position of the instrument tip at the pivot point, the determined position of the instrument tip model within the indentation model allows determining the instrument model coordinate system, InstModel, in relation to the indentation model that is a better estimation of the real position of the instrument tip within the indentation. Thus, using the determined instrument tip coordinate system in relation to the indentation model, and thus an origin of this instrument tip coordinate system in relation to the indentation model, the medical instrument is calibrated in an improved way.

Thus, the calibration of the instrument can be improved. Consequently, the tracking of the instrument can be improved.

According to another exemplary embodiment of the present invention, calibrating the medical instrument comprises determining an instrument-marker-to-instrument-tip-coordinate-transformation, InstMarkerToInstTip, which describes a transformation between an instrument marker coordinate system, InstMarker, and an instrument tip coordinate system, InstTip, thereby using the determined instrument model coordinate system, InstModel.

Preferably, the instrument marker coordinate system is the coordinate system that is defined by the instrument marker positions and orientations of the marker array used by the tracking system for tracking.

Preferably, the instrument tip coordinate system is the coordinate system that is defined by the instrument tip as origin and by the spatial orientation of the instrument using the longitudinal instrument axis and another perpendicular axis.

As described, the goal of calibration of the instrument is making a statement about the position and orientation of the instrument marker in relation to the position and orientation of the instrument tip coordinate system. In other words, at the end of the calibration, a relationship between the instrument marker coordinate system, InstMarker, and the instrument tip coordinate system, InstTip, is determined. This relationship is described by the instrument-marker-to-instrument-tip coordinate-transformation, InstMarkerToInstTip.

However, instead of using the relationship between the instrument tip and the calibration device pivot point as indicator for the instrument tip, the determined transformation between instrument model coordinate system, InstModel, in relation to an indentation model coordinate system, which is identical to the calibration device coordinate system, is used for describing the relationship between the instrument tip and the calibration device. Thus, a more accurate estimation of the position of the instrument tip within the indentation of the calibration device is the basis of the calibration of the instrument.

Thus, the calibration of the instrument can be improved. Consequently, the tracking of the instrument can be improved.

According to another exemplary embodiment of the present invention, calibrating the medical instrument comprises providing a calibration-device-to-instrument-tip-coordinate-transformation, CalDevToInstTip, which describes a transformation between a calibration device coordinate system, Cal, and the instrument tip coordinate system, InstTip, and determining the instrument-marker-to-instrument-tip-coordinate-transformation, InstMarkerToInstTip, thereby using the calibration-device-to-instrument-tip-coordinate-transformation, CalDevToInstTip.

Preferably, the calibration device coordinate system is the coordinate system that is defined by the calibration device, in particular a calibration marker of the calibration device used by the tracking system for tracking.

Thus, a calibration-device-to-instrument-tip-coordinate-transformation, CalDevToInstTip, being a transformation between the calibration device coordinate system and the instrument tip coordinate system, is determined. CalDevToInstTip is determined, thereby using a camera-to-calibration-device-coordinate-transformation, CamToCalDev, being a transformation between the camera coordinate system and the calibration device coordinate system, an instrument-marker-to-camera-coordinate-transformation, InstMarkerToCam, being a transformation between the instrument marker coordinate system and the camera coordinate system, and an instrument-tip-to-instrument-marker-coordinate-transformation, InstTipToInstMarker, being a transformation between the instrument tip coordinate system and the instrument marker coordinate system.

Equation 1 describes this relationship:

$$InstTipToCalDev = CamToCalDev * InstMarkerToCam * InstTipToInstMarker \quad (1):$$

The instrument-tip-to-calibration-device-coordinate-transformation, InstTipToCalDev, is the inverted transformation to the determined CalDevToInstTip transformation.

Consequently, the instrument-marker-to-instrument-tip-coordinate-transformation, InstMarkerToInstTip, is the inverted transformation to the to be determined instrument-tip-to-instrument-marker-coordinate-transformation, InstTipToInstMarker.

The matrix multiplication reads from right to left, in other words, A*B*C means first applying C, then B then A.

As described, this transformation might be erroneous due to wrongly disposing the origin of the instrument tip coordinate system onto the deepest point of the indentation, also called pivot point. With the help of the instrument model, an instrument model coordinate system is introduced, used for correcting the origin of the instrument tip coordinate system, or in other words, the position of the instrument tip.

In the described case, the instrument-marker-to-instrument-tip-coordinate-transformation, InstMarkerToInstTip, is unknown and needs to be determined. In other words, it is not known due how the instrument tip is positioned in relation to the instrument marker. By rearranging equation 1, to InstMarkerToInstTip, equation 2 reads:

InstMarkerToInstTip=CalDevToInstTip*
CamToCalDev*InstMarkerToCam    (2)

The calibration-device-to-instrument-tip-coordinate-transformation, CalDevToInstTip, normally is determined as described by holding the instrument tip into the indentation and assume that the instrument tip is located at the pivot point of the indentation. In particular, CalDevToInstTip is defined from instrument tip in calibration device coordinates and three axes in calibration device coordinates.

In this case, the calibration-device-to-instrument-tip-coordinate-transformation is determined by matching the instrument tip model onto the indentation model. In other words, instead of using the pivot point of the indentation of the calibration device, which is the commonly used reference point of the instrument tip, as an origin of the instrument tip coordinate system, by matching the instrument tip model onto the indentation model, an updated origin of the instrument tip coordinate system, being the origin of the instrument model coordinate system, also called updated reference point, can be determined.

Thus, the calibration of the instrument can be improved. Consequently, the tracking of the instrument can be improved.

According to another exemplary embodiment of the present invention, calibrating the medical instrument comprises providing an instrument-model-to-instrument-tip-coordinate-transformation, InstModelToInstTip, which describes a transformation between the instrument model coordinate system, InstModel, and the instrument tip coordinate system, InstTip, and it comprises providing a calibration-device-to-instrument-model-coordinate-transformation, CalDevToInstModel, which describes a transformation between the calibration device coordinate system, CalDev, and the instrument model coordinate system, InstModel and determining the calibration-device-to-instrument-tip-coordinate-transformation, CalDevToInstTip, thereby using the instrument-model-to-instrument-tip-coordinate-transformation, InstModelToInstTip, and the calibration-device-to-instrument-model-coordinate-transformation, CalDevToInstModel.

In other words, the calibration-device-to-instrument-tip-coordinate-transformation, CalDevToInstTip, being the transformation between the calibration device coordinate system and the instrument tip coordinate system, is determined by multiplying the calibration-device-to-instrument-model-coordinate-transformation, CalDevToInstModel, being the transformation between the calibration device coordinate system and the instrument model coordinate system, with the instrument-model-to-instrument-tip-coordinate-transformation, InstModelToInstTip, being the transformation between the instrument model coordinate system and the instrument tip coordinate system.

Equation 3 describes this relationship:

CalDevToInstTip=InstModelToInstTip*CalDevToInstModel    (3):

The position and orientation of the indentation of the calibration device is already known in relation to the coordinate system of the markers of the calibration device. Manufacturing tolerances and tracking errors of the calibration device are small enough to be neglected in comparison to the instrument. In other words, a coordinate system of the calibration device model matches the coordinate system of the calibration device, so that no transformation is needed. Consequently, an indentation coordinate system also matches the coordinate system of the calibration device and the calibration device model.

Thus, the calibration of the instrument can be improved. Consequently, the tracking of the instrument can be improved.

According to another exemplary embodiment of the present invention, matching the instrument tip model onto the indentation model comprises determining the calibration-device-to-instrument-model-coordinate-transformation, CalDevToInstModel, thereby using the determined instrument model coordinate system in particular in indentation coordinates or equivalently in calibration device coordinates.

In other words, instead of the pivot point, also called reference point, of the indentation of the calibration device as an origin of the instrument tip coordinate system, by matching the instrument tip model onto the indentation model, an updated origin of the instrument tip coordinate system, being the origin of the instrument model coordinate system, also called updated reference point, can be determined.

Thus, the calibration of the instrument can be improved. Consequently, the tracking of the instrument can be improved.

According to another exemplary embodiment of the present invention, the method comprises the step of determining an actual spatial orientation of the instrument, preferably along an axis of the instrument and of using said determined actual spatial orientation during matching the instrument tip model onto the calibration device model.

The actual spatial orientation of the instrument preferably relates to an angle, in which the instrument is arranged in the indentation.

The term "actual spatial orientation" relates to the current spatial orientation.

The spatial orientation preferably comprises the position of the instrument. Further preferably, it is always kept track of the instrument tip and an instrument handle as well as three axes of the instrument. For example, the Instrument features a pre-calibrated axis, but the instrument tip still has to be calibrated. In this case, the axis of the instrument has to be intersected with a plane on the calibration device so a good estimation of the length of the instrument can be achieved. The length of the instrument is used to check the distance of the instrument to the indentation of the calibration device.

In case the instrument is pre-calibrated, the original instrument coordinate system is known in relation to the instrument tip. But in case the instrument is not pre-calibrated, an axis is calibrated first in a preceding workflow step. Then, the axis is projected onto the calibration device and the instrument coordinate system origin is determined as reference point in the first camera frame of the calibration. Once determined, the reference point is not updated any more. In other words, it can be reset because the calibration is automatically started by a heuristic and this can go wrong, so the calibration process is restarted as well. Therefore, the origin of the instrument coordinate system can be defined for instruments without pre-calibration and corrected in the same way as for pre-calibrated instruments. This correction with averaging is described as follows.

In order to correct the instrument coordinate system's position in relation to the instrument tip coordinate system using averaging, a difference vector between the original, pre-calibrated or projected, instrument coordinate system and the newly calculated instrument coordinate system is calculated. If transformations are given as 4×4 matrices, the difference vector is calculated as:

diffVector=NewInstrumentTipToInstMarker·(0,0,0,1)$^T$−OriginalInstTipToInstMarker·(0,0,0,1)$^T$ Thus, the origin of the instrument tip coordinate system, which is the reference point, is transformed into instrument marker coordinates through original and newly found instrument-tip-to-instrument-marker-coordinate-transformation, InstTipToInstMarker. The difference vector is therefore given in instrument marker coordinates.

All of these steps are performed for each camera frame. Thus for many frames, a lot of difference vectors are calculated and, for averaging, the vectors are stored in a 2D array of discrete camera angle-dependent error vectors, in other words a list of vectors, referring to spherical coordinates as follows:

diffVectors[polarAngle][longitudeAngle]={list of vectors}

The variables polarAngle and longitudeAngle are calculated using the vector from marker center to camera center according to spherical coordinates applied on the marker.

Both angles are calculated once for the entire marker array at a specific point within the three markers, not for each marker. As an example, if the marker array is seen at 45 degrees polar angle and 320 degrees longitude in three camera frames, then at 46 degrees polar angle in one frame, the corresponding difference vectors are stored:

diffVectors[45][320]={(0.12,0.52,0.72),(0.2,0.45, 0.65),(0.17,0.63,0.63)} diffVectors[46][320]={(0.15,0.54,0.62)}

Preferably, a smaller array diffVectors, one entry per 10 degrees, is used, because it covers the marker errors well enough. When sufficient elements of the array over different polar coordinates are filled with a sufficient number of vectors, the medians of the vector components are calculated for each list to provide a stable average value for the angle-dependent error.

The overall averaged difference vector is determined by each component of the vector taking the mean of all the calculated medians for that component. This vector is eventually used to determine the averaged instrument-marker-to-instrument-tip-coordinate-transformation, InstMarkerToInstTip.

According to another exemplary embodiment of the present invention, the actual spatial orientation is determined based on a result of tracking the instrument.

Thus, the determination of the actual spatial orientation of the instrument is further improved.

According to another exemplary embodiment of the present invention, the method comprises the step of determining the actual spatial orientation based on an estimation of the axis of the instrument and/or based on learning from a rotation movement of the instrument tip in the indentation, which is recorded by a tracking device.

In a preferred embodiment, the actual spatial orientation is determined based on a calibration of the axis of the instrument. Thus, the position of the instrument tip and the instrument handle can be determined. Knowing the position and/or the extent of the axis of the instrument allows for an improved determination of the actual spatial orientation of the instrument. The position of the axis of the instrument might also be known from a stored pre-calibration of the axis of the instrument. Additionally, the position of the axis of the instrument can be derived from knowing a tracker location and orientation of the instrument.

Thus, the determination of the actual spatial orientation of the instrument is further improved.

Preferably, the method comprises the step of measuring, calibrating, validating and/or verifying the medical instrument using the estimated position of the instrument tip as an updated reference point.

Measuring the instrument preferably comprises determining data of the shape of the individual medical instrument currently used by the doctor.

Calibrating the instrument preferably comprises updating data stored in the navigation system about the shape of the individual medical instrument and/or about the reference point of the calibration device, which is the estimated position of the instrument tip as well as determining the axis of the instrument. Thus, the tip, the axis near the tip and the axis between the tip and the instrument handle is calibrated. Furthermore, the instrument tip model is also calibrated. Calibrating further comprises finding the axis of the instrument. At many shapes of the instrument, in particular curved instruments there is no generic relation between shape of the instrument and axis of the instrument. Thus, preferably the instrument tip, the axis near the instrument tip, in particular for the elongation of the instrument, and the axis between the instrument tip and the instrument handle is stored and calibrated. Additionally, the shape of the 3D model is also calibrated, wherein the user for example puts the instrument onto a pre-defined plane on the calibration device, so the instrument is assumed to be a flat tip, chisel tip, tap or screw depending on the location on the calibration device.

Validating the instrument preferably comprises determining if the estimated position of the instrument tip corresponds to the position of the instrument tip according to the tracking device.

Verifying the instrument preferably comprises determining the discrepancy between the estimated positon of the instrument tip and the position of the instrument tip according to the tracking device. This may comprise a comparison with a pre-defined threshold value to reflect deviations acceptable for a doctor or a surgical navigation system.

According to another exemplary embodiment of the present invention, the method comprises the step of generating a plurality of frames of different positions of the instrument tip in the indentation by using a surgical navigation device. Furthermore, matching the instrument tip model onto the calibration device model for each frame and determining a position of the instrument tip model within the indentation model for each frame. The method further comprises the step of calculating an average position of the instrument tip model based on the determined positions of the instrument tip model of every frame.

Thus, the determination of the position of the instrument tip model is repeated for a plurality of frames during the calibration process.

The markers, in particular infrared-reflecting passive markers, are often significant contributors to the overall error near the instrument tip. While the calibration device provides a marker array with the indentation near the array, the instrument tip is located comparably far from the instrument marker array, so rotational errors in the camera-to-instrument-marker-coordinate-transformation cause higher errors at the tip. In other words, the positional error at the instrument tip increases linear with the distance to the marker array. There is small positional error of high frequency on the marker position which needs to be averaged over several camera frames. Bigger errors come from observations of the markers depending on their angle towards the camera, so the user is typically guided to rotate the instrument in the pivot point to provide angle-dependent information for many camera frames.

Preferably, determined positions of the instrument tip model outside of a predetermined standard deviation may not be considered.

The plurality of frames is around or larger than 100 frames.

Preferably, the instrument tip is rotated within the indentation of the calibration device. Further preferably, the instrument tip is rotated within the indentation of the calibration device until a stop criterion is met. The stop criterion preferably is met after the rotation of the instrument tip of a predetermined angle, when a predetermined amount of frames within a predetermined standard deviation is determined and/or when a predetermined amount of consecutive frames outside of the predetermined standard deviation are determined.

The reference point of the calibration device model correlates to a predetermined ideal position of the instrument tip in the indentation. In a cone shaped or pyramid shaped indentation of the calibration device the predetermined ideal position of the instrument tip preferably is the tip of the cone shape.

Preferably, the instrument tip is rotated within the indentation of the calibration device, thereby generating a plurality of frames of different positions of the instrument tip in the indentation by using a surgical navigation device. Preferably, different angles leading to different positions of the instrument tip are necessary while generating the frames.

Preferably, the method comprises the step of using the calculated average position of the instrument tip as an updated reference point in a surgical navigation system.

Thus, the accuracy of the surgical navigation system can be improved.

According to another exemplary embodiment of the present invention, the matching of the models comprises the step of calculating, based on the instrument tip model and the calibration device model, at least one collision point between the instrument tip model and the calibration device model. Furthermore, the method comprises determining the position of the instrument tip model within the indentation model, thereby using the at least one collision point.

In order to estimate the real position of the instrument tip in the indentation of the calibration device, collision points have to be found. The collision points relate to the points, where the calibration device and the instrument tip touch, when the instrument tip is arranged within the indentation of the calibration device.

Using the collision points and the thus determined position of the instrument tip model within the indentation model of the calibration device model, the instrument model coordinate system, InstModel is determined in relation to the indentation model. Consequently, the calibration-device-to-instrument-model-coordinate-transformation, CalDevToInstModel between the calibration device coordinate system of the calibration device and the instrument model coordinate system is determined.

In other words, the collision points define the position of the instrument tip model within the indentation model. The updated reference point is consequently defined by the predetermined reference point in the instrument model at the position of the instrument compared to the position of the indentation.

According to another exemplary embodiment of the present invention, the method comprises the step of placing the instrument tip model onto a reference point of the calibration device model. Furthermore, executing an elevation step, thereby elevating the instrument tip model onto the indentation model along a base axis perpendicular to a surface of the calibration device model, thereby determining a first collision point. The method further comprises the step of executing at least one first descending step, thereby shifting the instrument tip model onto the indentation model along a known gradient of the indentation from the first collision point towards the reference point of the calibration device, thereby determining a second collision point and a shifted first collision point.

Shifting the instrument tip model comprises storing and collecting all shift transformations and interpreting the original surface points in transformed coordinates. Preferably, a shifting vector is determined for every step, like elevation and/or descending, and the whole instrument tip model is shifted.

Preferably, the first collision point is shifted along the gradient of the indentation from towards the reference point of the calibration device onto a shifted first collision point. This shift is dependent on the first descending step.

Executing those steps, the instrument tip model and the indentation model are arranged in a fashion that relates to the reality of the instrument tip being disposed within the indentation. Since two collision points are found, a first determination of the position of the instrument tip model within the indentation model can be executed.

Preferably, the method comprises the step of executing at least one second descending step, thereby shifting the instrument tip model onto the indentation model along a gradient of the indentation from a centre point between the first collision point and the second collision point towards the reference point of the calibration device, thereby determining a third collision point.

According to another exemplary embodiment of the present invention, the method comprises the step of determining a third collision point by virtually shifting the instrument tip model onto the indentation model along a horizontal shifting vector, which is a projection of a gradient of the indentation model from a centre point between the shifted first collision point and the second collision point towards the reference point of the calibration device model in a horizontal plane through the centre point.

Furthermore, repositioning the instrument tip model to an average position between the shifted first collision point, the second collision point and the third collision point in the horizontal plane. The method further comprises the step of descending the instrument tip model onto the indentation model along the base axis, thereby determining a final collision point.

Virtually shifting the instrument tip model differs from shifting the instrument tip model by not actually shifting the instrument tip model, but determining a location of a certain point of the instrument tip model, if the instrument tip model actually would have been shifted. In this case, only the third collision point of the instrument tip model with the indentation model is important for further calculations. Therefore, the instrument tip model is not actually shifted but only virtually shifted.

Thus, an improved estimation for the instrument tip is found.

In a preferred embodiment, the horizontal plane is defined by the surface of the calibration device outside of the indentation.

Some instrument shapes might collide with the indentation when moving along the gradient of the indentation, although the global optimum for a collision point is not found, in particular when the starting point is not good.

However, by shifting the instrument tip in a horizontal plane, repositioning the instrument tip and descending the instrument tip along the base axis, an improved estimate of the position of the instrument tip can be found.

Preferably, the first descending step for determining the second collision point, the steps of repositioning and descending for determining the third collision point and the step of descending along the base axis for determining the final collision point can be repeated to iteratively find the optimal position of the instrument tip.

According to another exemplary embodiment of the present invention, the instrument tip model comprises a mesh of surface points, wherein the elevation of the instrument tip model onto the indentation model is determined by an elevation vector, wherein the elevation vector is the longest vector between the respective surface points of the instrument tip model and the indentation model along the base axis.

Thus an efficient way of determining the elevation amount of the elevation step is provided.

According to another exemplary embodiment of the present invention, the gradient of the indentation of the calibration device determines a common shifting direction vector towards the reference point of the calibration device. A shifting amount is determined by a shifting vector, wherein the shifting vector is the shortest vector between the respective surface points of the instrument tip model and the indentation model along the common shifting direction vector.

Thus an efficient way of determining the shifting amount of the descending steps is provided.

According to another exemplary embodiment of the present invention, the method comprises the step of determining a force vector correlating to an estimated force applied onto the instrument by a user based on the shape of the indentation. Furthermore, the method comprises the step of executing a force shifting step, shifting the instrument tip model onto the indentation model along the determined force vector.

In a preferred embodiment, a back shifting step is executed after the force shifting step, shifting the instrument tip model onto the indentation model along the gradient of the indentation towards the reference point of the indentation. The back shifting step further preferably relates to another first descending step.

In a preferred embodiment, the force shifting step is executed after determining the second collision point and/or after determining the third collision point.

Thus, the force used by the user of the instrument in order to hold the instrument tip within the indentation of the calibration device can be considered. Therefore, the determination of the estimated position of the instrument tip can be improved.

In a preferred embodiment of the present invention the shape of the indentation is a cone or a pyramid.

This is a shape of the indentation, which is optimized for the method of calibrating the instrument. Preferably, the shape of the indentation of the calibration device comprises a continuous gradient, allowing for intersecting the instrument tip model with the indentation model with a mathematically efficient algorithm and/or allowing for a fast descent search towards the reference point of the calibration device.

According to another exemplary embodiment of the present invention, the surface of the instrument model comprises a mesh of surface points, wherein the method comprises the step of optimizing the surface of the instrument model by reducing the surface of the instrument model to a relevant surface, by mesh optimization and/or by transforming the surface of the instrument model into a local coordinate system of the indentation.

The relevant surface of the instrument model preferably is determined by the length of the graduation of the indentation. Thus improving an intersection calculation performance.

According to the present disclosure, a use of the determined position of the instrument tip model, determined by a method, as disclosed herein, in a surgical navigation system is provided.

According to the present disclosure, an instrument calibration system comprising a medical instrument with a tracker and a tracking device, configured for tracking the tracker arranged on the medical instrument, the instrument calibration system being configured for executing the method, as described herein, is provided.

According to the present disclosure, a surgical navigation system for computer assisted surgery, the system comprising an instrument calibration system, as described herein, is provided.

According to the present disclosure, a computer program is provided, which, when running on a computer or when loaded onto a computer, causes the computer to perform the method steps of the method, as described herein. Furthermore, a program storage medium is provided, on which the program is stored. Furthermore, a computer is provided, comprising at least one processor and a memory and/or the program storage medium, wherein the program is running on the computer or loaded into the memory of the computer. A signal wave or a digital signal wave, carrying information which represents the program is provided. A data stream which is representative of the program is provided.

For example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal. The signal can be implemented as the signal wave which is described herein. For example, the signal, for example the signal wave is constituted to be transmitted via a computer network, for example LAN, WLAN, WAN, for example the internet. The invention according to the second aspect therefore may alternatively or additionally relate to a data stream representative of the aforementioned program.

In a third aspect, the invention is directed to a non-transitory computer-readable program storage medium on which the program according to the fourth aspect is stored.

BRIEF DESCRIPTION OF THE DRAWINGS

In the following, the invention is described with reference to the appended figures which give background explanations and represent specific embodiments of the invention.

The scope of the invention is however not limited to the specific features disclosed in the context of the figures, wherein FIG. 1 schematically shows transformations and coordinate systems in an instrument calibration system.

DESCRIPTION OF EMBODIMENTS

Figure 1:
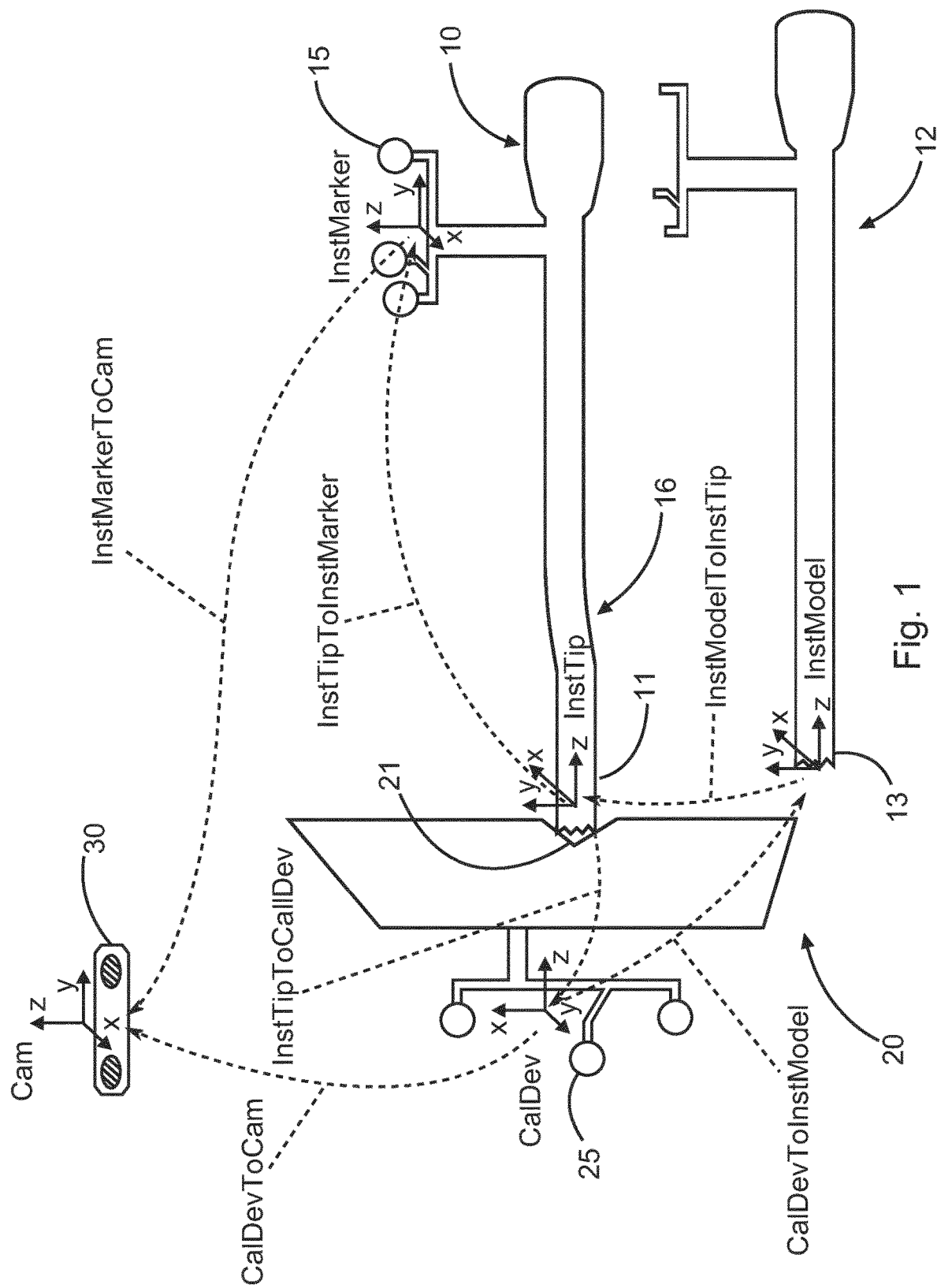

FIG. 1 describes a tracking setup for an instrument 10. For a calibration of the instrument 10, different coordinate systems of the participating objects need to be related to each other. The tracking setup comprises the medical instrument 10, a calibration device 20 and a tracking device 30. The tracking device 30 in this case is an infrared camera capable of detecting markers 15, 25 disposed at the instrument 10 and the calibration device 20, respectively.

Thus, the instrument 10 comprises an instrument marker 15 in form of a marker array of three infrared reflecting spheres. The instrument marker 15 is disposed at a handle side of the instrument 10 spaced apart from an instrument tip 11 of the instrument 10. The instrument marker 15 defines an origin of an instrument marker coordinate system InstMarker.

The calibration device 20 comprises a calibration marker 25 in form of a marker array of three infrared reflecting spheres. The calibration device 20 comprises at least one indentation 21, used for calibration of the instrument 10. The calibration device marker 25 is disposed relatively close to indentation 21 and defines an origin of a calibration device coordinate system CalDev.

The tracking device 30 defines an origin of a camera coordinate system Cam.

For tracking the instrument 10, the tracking device 30 tracks the instrument marker 15. However, due to different factors, like bending the instrument 10, the instrument tip 11 is not at an expected position compared to the instrument marker 15. In this case, as shown in FIG. 1, the instrument 10 does not have a straight axis in direction towards the instrument tip 11, rather the instrument 10 has a bend 16. This leads to a situation, wherein the instrument tip 11 is not located at an assumed position in relation to the instrument marker 15. Thus, the instrument tip 11 is calibrated by using the calibration device 20 before the instrument 10 is used for tracking. In other words, the instrument tip 11 defines an origin of an instrument tip coordinate system InstTip.

For calibrating the instrument 10, it is necessary to find a relationship between the instrument tip 11 and the calibration device 20. By holding the instrument tip 11 of the instrument 10 into the indentation 21 of the calibration device 20, a relationship between the position of the calibration device 20 and the instrument tip 11 is determined. Consequently, a relationship between the position of the instrument marker 15 and the instrument tip 11 can be determined.

In general, by holding the instrument tip 11 into the indentation 21, an instrument-tip-to-calibration-device-coordinate-transformation, InstTipToCalDev, being a transformation between the calibration device coordinate system Cal and the instrument tip coordinate system InstTip, is determined. InstTipToCalDev is determined by matrix multiplying a camera-to-calibration-device-coordinate-transformation, CamToCalDev, being a transformation between the camera coordinate system Cam and the calibration device coordinate system CalDev, an instrument-marker-to-camera-coordinate-transformation, InstMarkerToCam, being a transformation between the instrument marker coordinate system InstMarker and the camera coordinate system Cam, and an instrument-tip-to-instrument-marker-coordinate-transformation, InstTipToInstMarker, being a transformation between the instrument tip coordinate system InstTip and the instrument marker coordinate system InstMarker.

Equation 1 describes this relationship:

InstTipToCalDev=CamToCalDev*InstMarkerToCam*InstTipToInstMarker  (1):

The matrix multiplication reads from right to left, in other words, A*B*C means first applying C, then B then A.

All transformations are invertible, so for example, if the instrument-tip-to-calibration-device-coordinate-transformation InstTipToCalDev is known, consequently the calibration-device-to-instrument-tip-coordinate-transformation CalDevToInstTip is known. Consequently those invertible notations are also used.

The transformations define how the coordinates of one system transform into coordinates of another system. After getting the positions of the markers 15, 25 from the tracking device 30, an algorithm assigns the markers 15, 25, so the markers 15, 25 are identified and a coordinate system can be clearly defined for each marker array 15, 25. The marker positions of the marker array given by the tracking system are matched (e.g. "Kabsch algorithm") to expected positions of the marker array.

When the instrument tip 11 however does not ideally fit into the indentation 21, an error is introduced into the calibration method, as the relationship between the instrument tip 11 and the calibration device 20 is defined by the deepest point of the indentation, called pivot point. In other words, using the calibration device 20, the origin of the instrument tip coordinate system InstTip is assumed at the pivot point, which might deviate from the real position of the instrument tip 11. By introducing an instrument model 12 with an instrument tip model 13, relating to the instrument 10 and the instrument tip 11, respectively, an instrument model coordinate system InstModel is introduced, used for correcting the origin of the instrument tip coordinate system InstTip, or in other words, the position of the instrument tip 11. Consequently, a calibration model 22 with an indentation model 23, relating to the calibration device 20 and the indentation 21, respectively, is introduced.

Based on the described above, the instrument-marker-to-instrument-tip-coordinate-transformation, InstMarkerToInstTip, is unknown and needs to be determined. In other words, it is not known how the instrument tip 11 is positioned in relation to the instrument marker 15. By rearranging equation 1, to InstMarkerToInstTip, equation 2 reads:

InstMarkerToInstTip=CalDevToInstTip*CamToCalDev*InstMarkerToCam  (2)

The calibration-device-to-instrument-tip-coordinate-transformation, CalDevToInstTip, normally is determined as described by holding the instrument tip into the indentation and assuming that the instrument tip 11 is located at the pivot point of the indentation 21.

In this case, the calibration-device-to-instrument-tip-coordinate-transformation CalDevToInstTip is determined by matching the instrument tip model 13 onto the indentation model 23. In other words, instead of the pivot point of the indentation 21 of the calibration device 20, which is the commonly used reference point of the instrument tip 11, as an origin of the instrument tip coordinate system InstTip, by matching the instrument tip model 13 onto the indentation model 23, an updated origin of the instrument tip coordinate system, being the origin of the instrument model coordinate system InstModel, also called updated reference point, can be determined in indentation model coordinates. Thus, the accuracy of the calibration of the instrument 10 can be improved. Consequently, the tracking of the instrument 10 can be improved.

When calibrating the instrument 10 the calibration-device-to-instrument-tip-coordinate-transformation, CalDevToInstTip is determined by matrix multiplying an instrument-model-to-instrument-tip-coordinate-transformation, InstModelToInstTip, and a calibration-device-to-instrument-model-coordinate-transformation, CalDevToInstModel.

In other words, the calibration-device-to-instrument-tip-coordinate-transformation, CalDevToInstTip, being the transformation between the calibration device coordinate system CalDev and the instrument tip coordinate system InstTip, is determined by multiplying the calibration-device-to-instrument-model-coordinate-transformation, CalDevToInstModel, being the transformation between the calibration device coordinate system CalDev and the instrument model coordinate system InstModel, with the instrument-model-to-instrument-tip-coordinate-transformation, InstModelToInstTip, being the transformation between the instrument model coordinate system InstModel and the instrument tip coordinate system InstTip.

Equation 3 describes this relationship:

CalDevToInstTip=InstModelToInstTip*CalDevToInstModel  (3):

The position and orientation of the indentation 21 of the calibration device 20 is already known in relation to the coordinate system of the markers of the calibration device. Manufacturing tolerances and tracking errors of the calibration device are small enough to be neglected in comparison to the instrument. In other words, a coordinate system of the calibration device model matches the coordinate system of the calibration device, so that no transformation is needed. Generally the standard deviations of independent errors X, Y sum up as $\sigma_{X+Y}^2 = \sigma_X^2 + \sigma_Y^2$, so the highest error has squared influence on (and dominates) the overall error.

Thus, the calibration of the instrument can be improved. Consequently, the tracking of the instrument can be improved.

In equation 3, the calibration-device-to-instrument-model-coordinate-transformation, CalDevToInstModel is unknown. This is determined by the matching step of matching the instrument tip model 13 onto the indentation model 23. Thus, the instrument model coordinate system InstModel is determined using a determined position of the instrument tip model 13 and a calibration-device-to-instrument-model-coordinate-transformation, CalDevToInst- Model, is determined between the calibration device coordinate system CalDev and the instrument model coordinate system InstModel.

In other words, instead of using the pivot point, also called reference point, of the indentation 21 of the calibration device 20 as an origin of the instrument tip coordinate system InstTip, by matching the instrument tip model 13 onto the indentation model 23, an updated origin of the instrument tip coordinate system, being the origin of the instrument model coordinate system InstModel, also called updated reference point, can be determined in calibration device coordinates.

Thus, the calibration of the instrument can be improved. Consequently, the tracking of the instrument can be improved.

Figure 2:
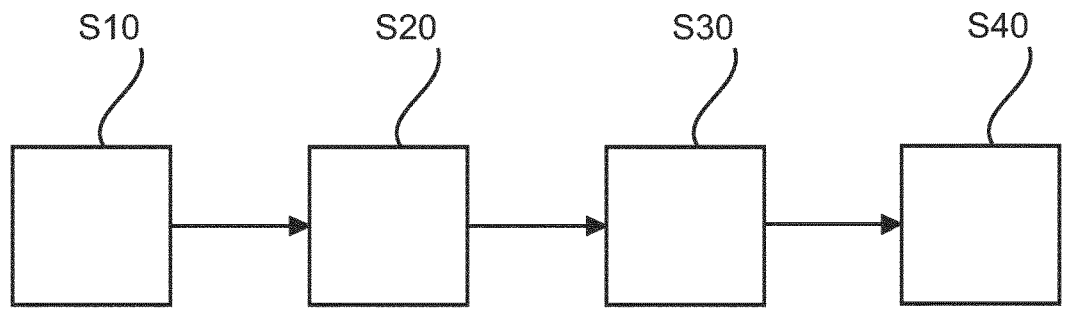
FIG. 2 schematically shows a flow diagram of the method of the present invention.

FIG. 2 illustrates the basic steps of the computer implemented medical method of calibrating a medical instrument 10. Step S10 encompasses providing an instrument model 12 comprising an instrument tip model 13, being a virtual model of a shape of a medical instrument 10 comprising an instrument tip 11. Step S20 encompasses providing a calibration device model 22 comprising an indentation model 23, being a virtual model of a shape of a calibration device 20 comprising an indentation 21 onto which the instrument tip 11 is introduced for calibration. Step S30 encompasses matching the instrument tip model 13 onto the calibration device model 23 thereby determining a position of the instrument tip model 13 within the indentation model 23, associated with an estimated position of the instrument tip 11 within the indentation 21. Step S40 encompasses calibrating the medical instrument 10, thereby using the determined position of the instrument tip model 13.

FIGS. 3a to 3f show different shapes of medical instrument tips 11 of a medical instrument 10. In order to use such an instrument 10 in a surgical navigation device, a tracking device needs to be able to track movements of the instrument 10. Therefore, in a first step, the instrument 10 needs to be calibrated in view of a tracking device 30. For this purpose, a calibration device 20 comprising at least one tracker is used for calibrating the instrument 10, which also comprises at least one tracker. During calibration of the instrument tip 11, the instrument 10 is held into the indentation 21 so the instrument tip 11 can be held in a fixed position regarding its own tracker and the tracked calibration device 20. In this exemplary embodiment, the indentation 21 has a cone shaped form extending from a surface of the calibration device 20 into the calibration device 20. When the instrument tip 11 is held into the indentation 21, the tracking device assumes that the instrument tip 11 is held in a fixed position at a reference point P. The reference point P in this case is the deepest point of the cone shaped indentation.

As described above, there are many instruments 10 and instrument tips 11 that do not fit in any provided indentation 21 on the calibration device 20. Therefore, the reference point P relating to the tip of the indentation 21 does not accurately reflect the real position of the instrument tip 11.

Figures 3A, 3B, 3C:
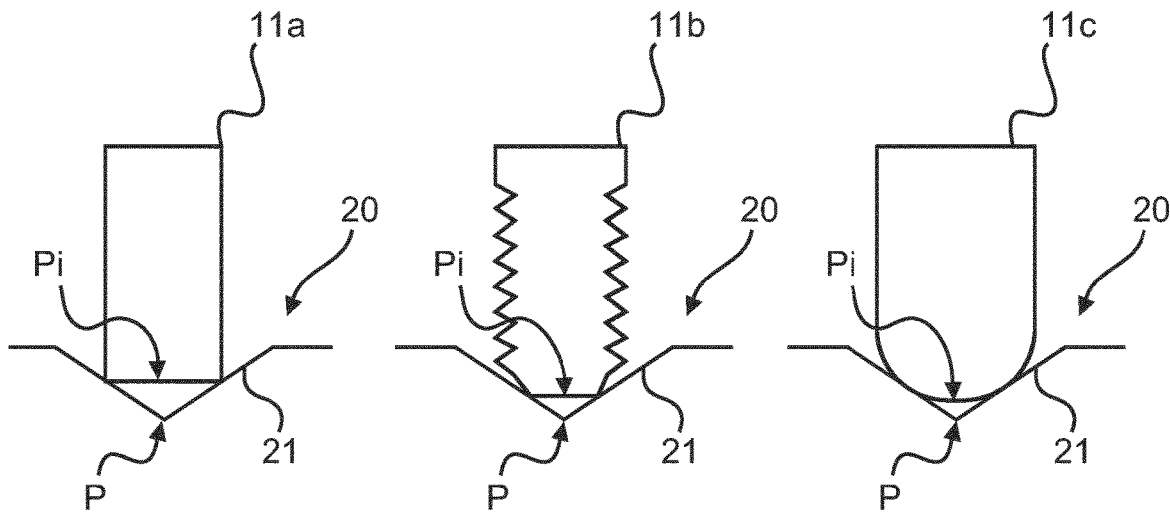
FIG. 3a schematically shows a medical instrument tip in accordance to a first embodiment.
FIG. 3b schematically shows a medical instrument tip in accordance to a second embodiment.
FIG. 3c schematically shows a medical instrument tip in accordance to a third embodiment.

FIG. 3a schematically shows an instrument tip 11a in accordance to a first embodiment. The instrument tip 11a is cylinder shaped. In order to calibrate the instrument tip 11a with the calibration device 20, a predetermined reference tip point of the instrument tip 11a needs to be located by a tracking device. This is achieved by holding the instrument tip 11a into the indentation 21. The predetermined reference tip point of the instrument tip 11a for example lies in the centre of the bottom plane of the cylinder. It is then assumed that the predetermined reference tip point of the instrument tip 11a matches the reference point P of the calibration device. As can be seen, the instrument tip 11a does not perfectly fit into the indentation 21. Therefore, as illustrated, the reference point P of the calibration device 20 relating to the tip of the indentation 21 does not match a real position of the predetermined reference tip point of the instrument tip 11a very well. Therefore, an updated reference point Pi is determined, better reflecting the real position of the instrument tip 11a and its reference tip point. When holding the instrument perpendicular to the surface of the calibration device 20 into the indentation 21, the real position of the reference tip point of the instrument tip 11a would lie in the deepest point of the cylinder in the indentation 21. The real position differs from the reference point P. Holding the instrument in another angle to the surface of the calibration device 20 might change the real position in the indentation 21 depending on the shape of the instrument tip 11a. The distance between the reference point P of the indentation and the real position of the reference tip point relates to a systematic error, the tracking device of the surgical navigation system faces, when assuming the position of the instrument tip 11 dependent on the reference point P. Thus, during calibration of the instrument 10, the location of the instrument tip 11a within the indentation 21 is better reflected by an updated reference point Pi, replacing the reference point P. The updated reference point Pi thereby relates to the position of the reference tip point of the instrument tip 11a, when the instrument tip 11a is held into the indentation 21.

FIG. 3b schematically shows an instrument tip 11b in accordance to a second embodiment. The instrument tip 11b has the form of a threaded cylinder. The predetermined reference tip point of the instrument tip 11b for example lies in the centre of the bottom plane of the threaded cylinder. This instrument tip 11b does also not fit perfectly into the indentation 21. Therefore, as illustrated, the reference point P of the calibration device 20 relating to the tip of the indentation 21 does not match a real position of the predetermined reference tip point of the instrument tip 11b very well. Therefore, an updated reference point Pi is determined, better reflecting the real position of the instrument tip 11b and its reference tip point. When holding the instrument perpendicular to the surface of the calibration device 20 into the indentation 21, the real position of the reference tip point would lie in the deepest point of the threaded cylinder in the indentation 21. The real position differs from the reference point P. Holding the instrument in another angle to the surface of the calibration device 20 might change the real position in the indentation 21 depending on the shape of the instrument tip 11b. Thus, during calibration of the instrument 10, the location of the instrument tip 11b within the indentation 21 is better reflected by an updated reference point Pi, replacing the reference point P. The updated reference point Pi thereby relates to the position of the reference tip point of the instrument tip 11b, when the instrument tip 11b is held into the indentation 21.

FIG. 3c schematically shows an instrument tip 11c in accordance to a third embodiment. The instrument tip 11c has the form of a cylinder with a spherical ground shape. The predetermined reference tip point of the instrument tip 11c for example lies in the deepest point of the spherical ground shape. This instrument tip 11c does also not fit perfectly into the indentation 21. Therefore, as illustrated, the reference point P of the calibration device 20 relating to the tip of the indentation 21 does not match a real position of the predetermined reference tip point of the instrument tip 11c very well. Therefore, an updated reference point Pi is determined, better reflecting the real position of the instrument tip 11c and its reference tip point. When holding the instrument perpendicular to the surface of the calibration device 20 into the indentation 21, the real position would lie in the deepest point of the spherical ground shape in the indentation 21. The real position differs from the reference point P. Holding the instrument in another angle to the surface of the calibration device 20 might change the real position in the indentation 21 depending on the shape of the instrument tip 11*c*. Thus, during calibration of the instrument 10, the location of the instrument tip 11*c* within the indentation 21 is better reflected by an updated reference point Pi, replacing the reference point P. The updated reference point Pi thereby relates to the position of the reference tip point of the instrument tip 11*c*, when the instrument tip 11*c* is held into the indentation 21.

Figures 3D, 3E, 3F:
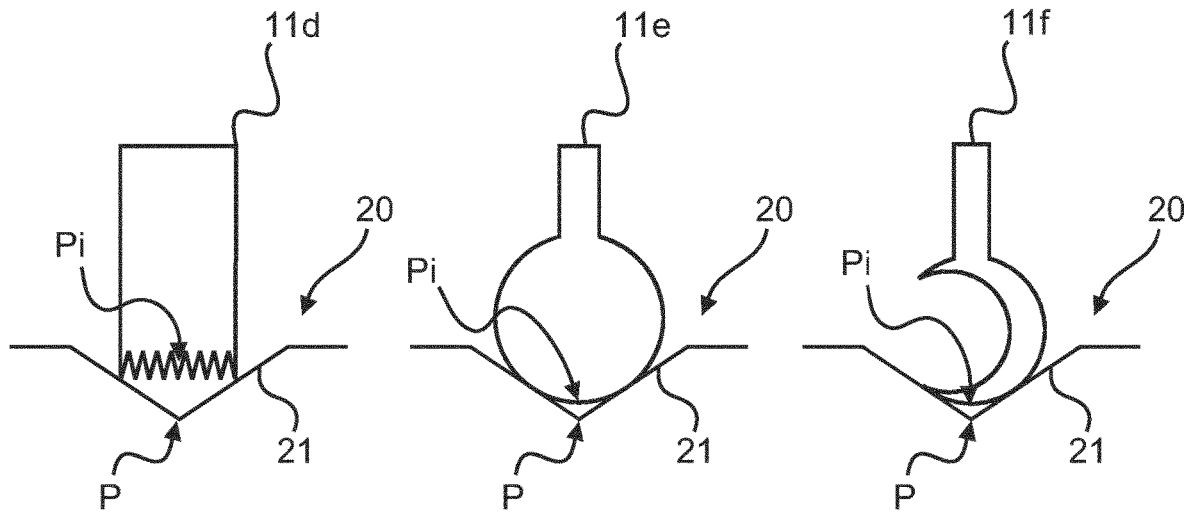
FIG. 3d schematically shows a medical instrument tip in accordance to a fourth embodiment.
FIG. 3e schematically shows a medical instrument tip in accordance to a fifth embodiment.
FIG. 3f schematically shows a medical instrument tip in accordance to a sixth embodiment.

FIG. 3*d* schematically shows an instrument tip 11*d* in accordance to a fourth embodiment. The instrument tip 11*d* has the form of a cylinder with a toothed ground shape. The predetermined reference tip point of the instrument tip 11*d* for example lies in the centre of the bottom plane of the toothed ground. This instrument tip 11*d* does also not fit perfectly into the indentation 21. Therefore, as illustrated, the reference point P of the calibration device 20 relating to the tip of the indentation 21 does not match a real position of the predetermined reference tip point of the instrument tip 11*d* very well. Therefore, an updated reference point Pi is determined, better reflecting the real position of the instrument tip 11*d* and its reference tip point. When holding the instrument perpendicular to the surface of the calibration device 20 into the indentation 21, the real position would lie in the deepest point of the toothed ground shape in the indentation 21. The real position differs from the reference point P. Holding the instrument in another angle to the surface of the calibration device 20 might change the real position in the indentation 21 depending on the shape of the instrument tip 11*d*. Thus, during calibration of the instrument 10, the location of the instrument tip 11*d* within the indentation 21 is better reflected by an updated reference point Pi, replacing the reference point P. The updated reference point Pi thereby relates to the position of the reference tip point of the instrument tip 11*d*, when the instrument tip 11*d* is held into the indentation 21.

FIG. 3*e* schematically shows an instrument tip 11*e* in accordance to a fifth embodiment. The instrument tip 11*e* has the form of a sphere. The predetermined reference tip point of the instrument tip 11*d* for example lies in the deepest point of the sphere. This instrument tip 11*e* does also not fit perfectly into the indentation 21. Therefore, as illustrated, the reference point P of the calibration device 20 relating to the tip of the indentation 21 does not match a real position of the predetermined reference tip point of the instrument tip 11*e* very well. Therefore, an updated reference point Pi is determined, better reflecting the real position of the instrument tip 11*e* and its reference tip point. When holding the instrument perpendicular to the surface of the calibration device 20 into the indentation 21, the real position would lie in deepest point of the sphere in the indentation 21. The real position differs from the reference point P. Holding the instrument in another angle to the surface of the calibration device 20 might change the real position in the indentation 21 depending on the shape of the instrument tip 11*e*. Thus, during calibration of the instrument 10, the location of the instrument tip 11*e* within the indentation 21 is better reflected by an updated reference point Pi, replacing the reference point P. The updated reference point Pi thereby relates to the position of the reference tip point of the instrument tip 11*e*, when the instrument tip 11*e* is held into the indentation 21.

FIG. 3*f* schematically shows an instrument tip 11*f* in accordance to a sixth embodiment. The instrument tip 11*f* has the form of a sickle. The predetermined reference tip point of the instrument tip 11*d* for example lies in the deepest point of the sickle. This instrument tip 11*f* does also not fit perfectly into the indentation 21. Therefore, as illustrated, the reference point P of the calibration device 20 relating to the tip of the indentation 21 does not match a real position of the instrument tip 11*f* very well. Therefore, an updated reference point Pi is determined, better reflecting the real position of the predetermined reference tip point of the instrument tip 11*f*. When holding the instrument perpendicular to the surface of the calibration device 20 into the indentation 21, the real position would lie in deepest point of the sickle in the indentation 21. The real position differs from the reference point P. Holding the instrument in another angle to the surface of the calibration device 20 might change the real position in the indentation 21 depending on the shape of the instrument tip 11*f*. Thus, during calibration of the instrument 10, the location of the instrument tip 11*f* within the indentation 21 is better reflected by an updated reference point Pi, replacing the reference point P. The updated reference point Pi thereby relates to the position of the reference tip point of the instrument tip 11*f*, when the instrument tip 11*f* is held into the indentation 21.

Figure 4A:
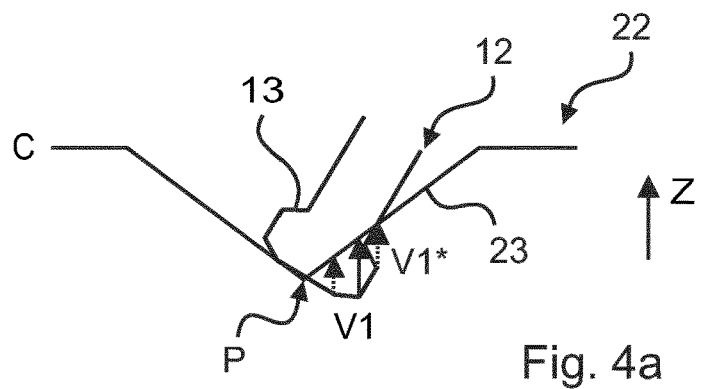
FIG. 4a schematically shows an instrument tip model and an indentation model of a calibration device model before an elevation step.

FIG. 4*a* shows an instrument model comprising an instrument tip model 13, being a virtual model of a shape of an instrument comprising an instrument tip 11. Additionally, FIG. 4*a* shows a calibration device model 22 comprising an indentation model 23, being a virtual model of a shape of a calibration device 20 comprising an indentation 21. For matching the instrument tip model 13 onto the calibration device model 22, in a first step, the instrument tip model 13 is placed onto a reference point P of calibration device model 22. In this exemplary embodiment, the instrument tip model 13 comprises a roughly cylindrically shaped end. The position of the instrument tip model 13 is hereby defined as the centre of the cylindrical ground surface of the end of the instrument tip model 13. Thus, the centre of the cylindrical ground surface of the end of the instrument tip model 13 is placed onto the reference point P. In this exemplary embodiment, the indentation is formed cone shaped. Therefore, the reference point P is the deepest point of the cone into the calibration device model 22.

After placing the instrument tip model 13 onto the reference point P, an elevation step is executed. The instrument tip model 13 is elevated on the indentation model 23 along a base axis Z. The base axis Z is defined perpendicular to the surface C of the calibration device model 22 outside of the indentation model 23. The elevation amount, which the instrument tip model 13 is elevated until it hits the indentation model 23 is the maximum distance of all surface points of the surface C of the calibration device model 22 on a common elevation direction vector along the base axis Z. In other words, from a plurality elevation direction vectors V1* (dotted vectors) of different surface points of the instrument tip model 13 towards the indentation model 23 along the common elevation direction vector, the longest vector is determined to be an elevation vector V1, which defines the elevation amount, which the instrument tip model 13 is elevated onto the indentation model 23. Thus, the common elevation direction vector and the elevation direction vectors V1* only describes the direction of the vector, but does not include a length. In contrast, the elevation vector V1 describes a direction and a length of the vector.

Figure 4B:
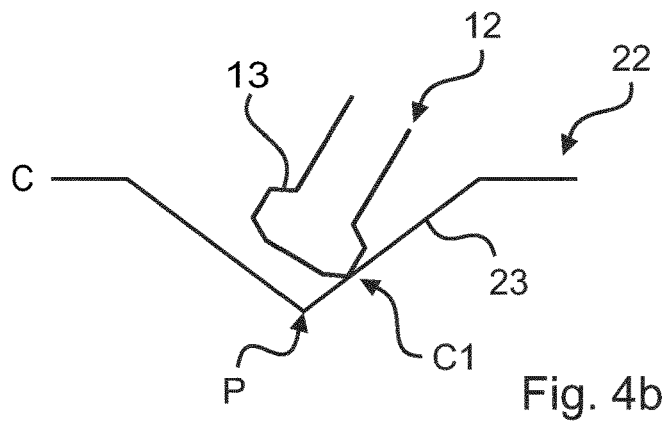
FIG. 4b schematically shows an instrument tip model and an indentation model of a calibration device model after an elevation step.

FIG. 4b shows the point, where the instrument tip model 13 collides with the indentation model 23 by the elevation step. This point is called first collision point C1.

Figure 5A:
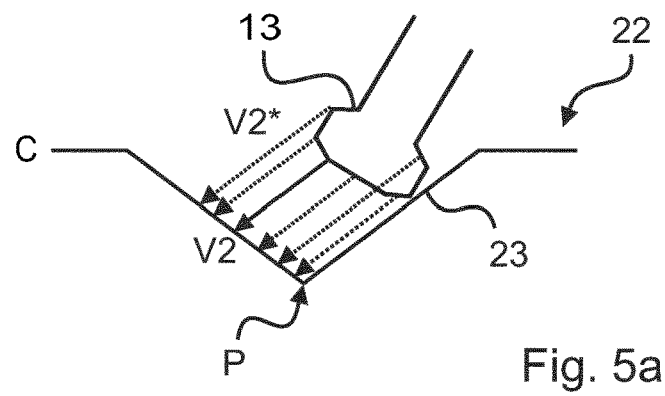
FIG. 5a schematically shows an instrument tip model and an indentation FIG. 5a model of a calibration device model before a first descending step.

FIG. 5a shows the next matching step. The instrument tip model 13 is shifted deeper into the indentation model 23. This step is called first descending step. The instrument tip model 13 is shifted onto the indentation model 23 along a known gradient of the indentation model 23 from the first collision point C1 towards the reference point P of the calibration device model 22. The vectors shown in FIG. 5a represent the gradient of the indentation model 23 from different points of the instrument tip model 13. The shifting amount, which the instrument tip model 13 is shifted until it hits the indentation model 23 is the minimum distance of all surface points of the surface of the instrument tip model 13 on a common first shifting direction vector along the gradient of the indentation model 23. Thus, from all first shifting direction vectors V2* (dotted vectors) of different surface points of the instrument tip model 13 towards the indentation model 23 along the common first shifting vector, the shortest vector is determined to be a first shifting vector V2, which defines the shifting amount, which the instrument tip model 13 is shifted onto the indentation model 23. In this case, the indentation model 23 has the shape of a cone. The distances can be calculated by defining a line through each surface point with direction of the common first shifting direction vector and by intersecting these lines with the indentation model 23. Thus, dependent on the shape of the indentation model 23, the mathematical formula for intersecting the line with the cone shape can be simplified in the local coordinate system. In this exemplary embodiment, wherein the shape of the indentation model 23 has a fixed gradient from the first collision point C1 to the reference point P, a second collision point C2 can be found in one descending step.

Figure 5B:
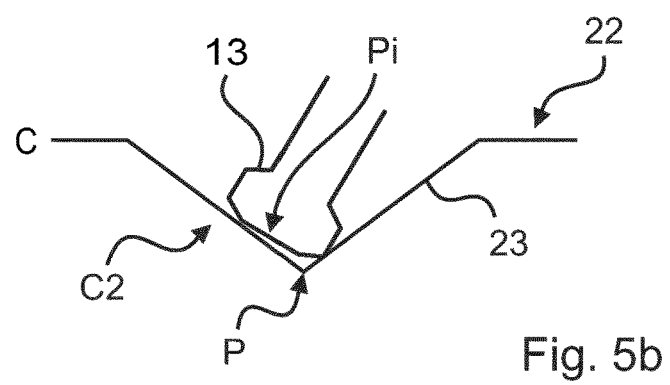
FIG. 5b schematically shows an instrument tip model and an indentation model of a calibration device model after a first descending step.

FIG. 5b shows the point, where the instrument tip model 13 collides with the indentation model 23 by the first descending step. This point is called second collision point C2. Based only on the first collision point C1 and the second collision point C2, a first determination of the position of the instrument tip model 13 can be done. When the position of the instrument tip model 13 within the indentation model 23 is determined, a location of an updated reference point Pi is determined. The difference between the reference point P, referring to the assumed position of the instrument tip 11 within the indentation 21, and the updated reference point Pi shows, how far away the determined position of the instrument tip model 13 is from the reference point P and how big of an error has been introduced into the calibration method of the prior art. This difference preferably is described by a difference vector resulting of a subtraction of the origin of the instrument tip model coordinate system from the pivot point of the calibration device model coordinate system in the same coordinates. Consequently, the instrument 10 is calibrated, thereby using the determined position of the instrument tip model 13 within the indentation model 23.

In FIGS. 6 to 10a more detailed view of the matching steps is illustrated. In contrast to the illustrations of FIG. 4 to FIG. 5, which show an example, wherein the first descending step already gives a good estimate for the instrument model 13 being held into the indentation model 23, FIG. 6 to FIG. 10 illustrate a more problematic example of a triangular instrument tip model 13, wherein more steps are necessary to fit the instrument tip model 13 into the indentation model 23.

Figure 6A:
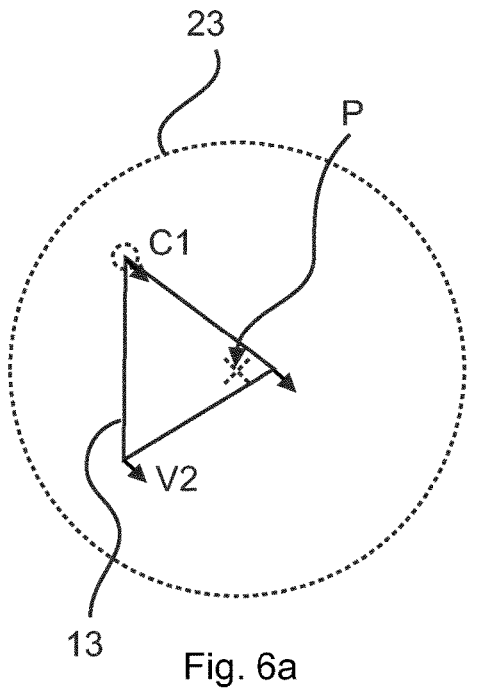
FIG. 6a schematically shows a top view of an instrument tip model and an indentation model of a calibration device model before a descending step.
Figure 6B:
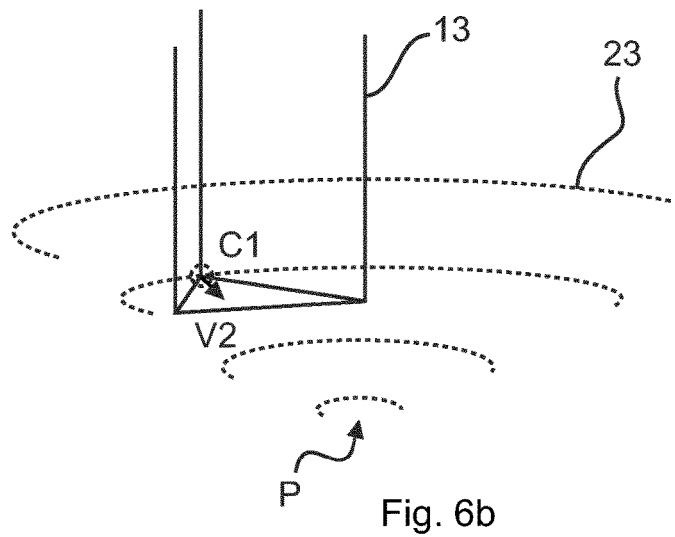
FIG. 6b schematically shows a perspective view of an instrument tip model and an indentation model of a calibration device model before a descending step.

FIG. 6a is a top view of the indentation model 23 and the instrument tip model 13. FIG. 6b is a perspective view of the same situation as illustrated in FIG. 6a. As can be seen from FIG. 6a and FIG. 6b, the instrument tip model 13 of this exemplary embodiment has the shape of an extruded triangle with a triangular ground shape. Additionally, the indentation model 23 has the shape of a cone. A tip of the cone shape marks the reference point P. FIG. 6a and FIG. 6b also already show the first collision point C1. Therefore, the elevating step has already been executed. Thus, the first descending step is shown. The instrument tip model 13 is shifted onto the indentation model 23 along the gradient of the indentation model 23 from the first collision point C1 towards the reference point P of the indentation model 23. The gradient of the indentation model 23 defines the plurality first shifting direction vectors (not shown). The point, where the instrument tip model 13 collides with the indentation model 23 along the first shifting direction vector (not shown) defines a second collision point C2. From all first shifting direction vectors (not shown) of different surface points of the instrument tip model 13 towards the indentation model 23 along the first shifting direction vector (not shown), the shortest vector is determined to be the first shifting vector V2, which defines the elevation amount, which the instrument tip model 13 is shifted onto the indentation model 23.

Figure 7A:
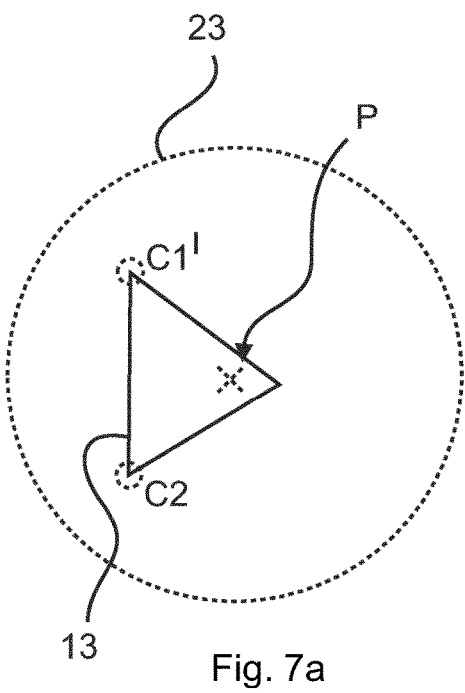
FIG. 7a schematically shows a top view of an instrument tip model and an indentation model of a calibration device model after a descending step.
Figure 7B:
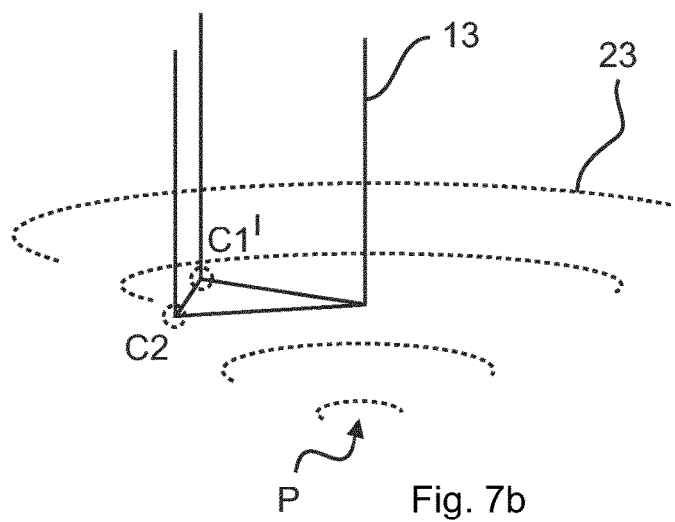
FIG. 7b schematically shows a perspective view of an instrument tip model and an indentation model of a calibration device model after a descending step.

FIG. 7a and FIG. 7b show the instrument tip model 13 and the indentation model 23 of FIG. 6a and FIG. 6b after the first descending step is finished. Since the instrument tip model 13 has been shifted along the gradient of the indentation model 23, the first collision point C1 has moved along the first shifting vector V2 onto a shifted first collision point C1'.

The illustrations of FIGS. 8a to 10b describe, how a third collision point C3 is determined.

Figure 8A:
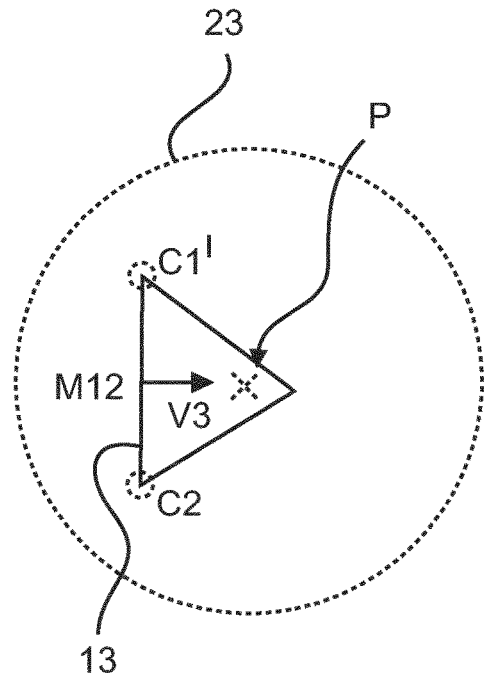
FIG. 8a schematically shows a top view of shifting an instrument tip model onto an indentation model of a calibration device model along a horizontal shifting vector.
Figure 8B:
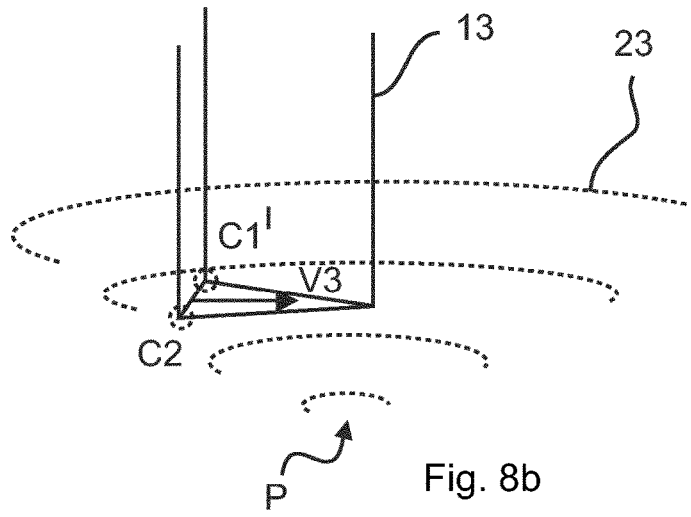
FIG. 8b schematically shows a perspective view of shifting an instrument tip model onto an indentation model of a calibration device model along a horizontal shifting vector.

FIG. 8a and FIG. 8b show the instrument tip model 13 and the indentation model 23 of FIG. 7a and FIG. 7b. Additionally, a horizontal shifting vector V3 is illustrated, indicating a shifting of the instrument tip model 13 onto the indentation model 23 along the horizontal shifting vector V3. A horizontal shifting direction vector (not shown) is determined by searching the centre point M12 between the shifted first collision point C1' and the second collision point C2. The horizontal shifting direction vector is then defined as the vector from the centre point M12 towards the reference point P, however projected into a horizontal plane through the centre point M12. The horizontal plane preferably extends parallel to the surface C of the calibration device model 22 outside of the indentation model 23. The third collision point C3 is found, when the instrument tip model 13 is shifted onto the indentation model 23. In other words, from all horizontal shifting direction vectors of different surface points of the instrument tip model 13 towards the indentation model 23 along the common horizontal shifting direction vector, the shortest vector is determined to be a horizontal shifting vector V3, which defines the shifting amount, which the instrument tip model 13 is shifted onto the indentation model 23.

Figure 9A:
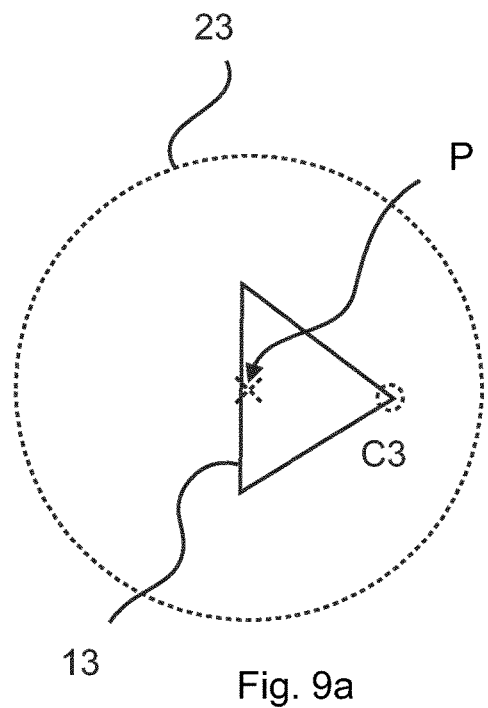
FIG. 9a schematically shows a top view of an instrument tip model and an indentation model after the horizontal shifting and before repositioning the instrument tip model to an average position between the shifted first collision point, the second collision point and the third collision point in the horizontal plane.
Figure 9B:
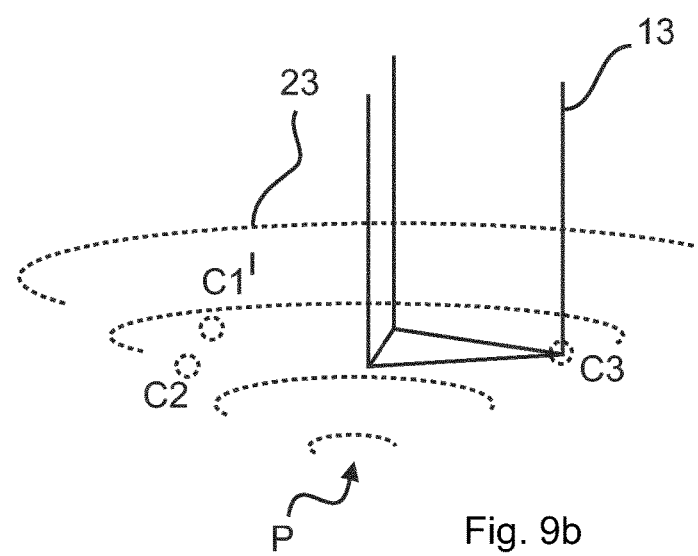
FIG. 9b schematically shows a perspective view of an instrument tip model and an indentation model after the horizontal shifting and before repositioning the instrument tip model to an average position between the shifted first collision point, the second collision point and the third collision point in the horizontal plane.

FIG. 9a and FIG. 9b show the instrument tip model 13 and the indentation model 23 of FIG. 8a and FIG. 8b after the instrument tip model 13 was virtually shifted along the horizontal shifting vector V3 onto the indentation model 23.

Figure 10A:
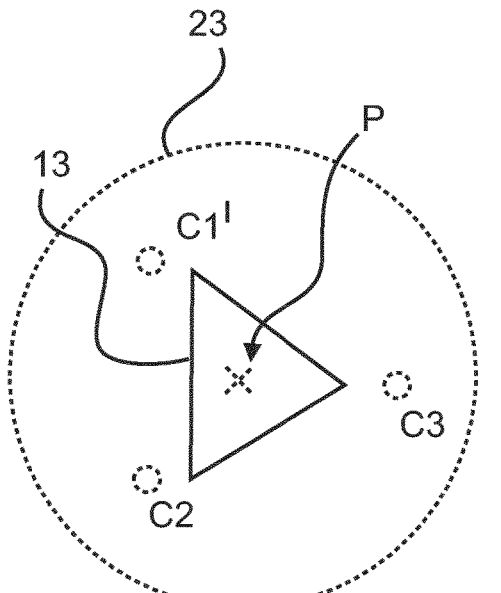
FIG. 10a schematically shows a top view of descending an instrument tip model onto an indentation model of a calibration device model along a base axis.
Figure 10B:
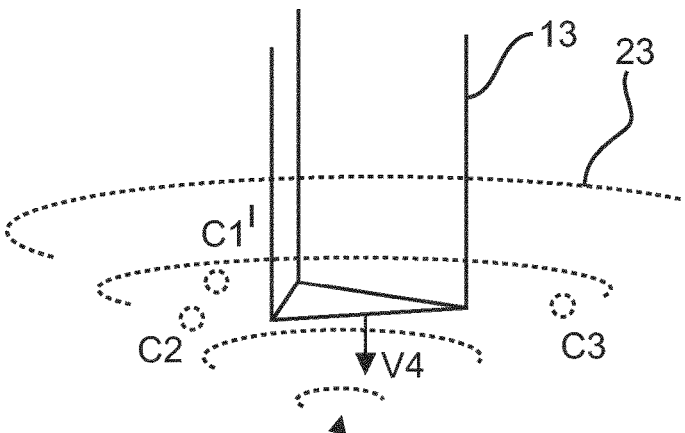
FIG. 10b schematically shows a perspective view of descending an instrument tip model onto an indentation model of a calibration device model along a base axis.

As illustrated in FIG. 10a and FIG. 10b, when the first collision point C1, in particular the shifted first collision point C1', the second collision point C2 and the third collision point C3 are defined, a repositioning step is executed, repositioning the instrument tip model 13 to an average position between the shifted first collision point C1', the second collision point C2 and the third collision point.

The average position between the shifted first collision point C1', the second collision point C2 and the third collision point is found in relation to the horizontal plane without a change of position of any of the collision points C1', C2 and C3 along the base axis Z. In this exemplary embodiment, the shifted first collision point C1', the second collision point C2 and the third collision point lie in the same horizontal plane since the instrument tip model 13 is held within the indentation model 23 perpendicular to the surface C of the calibration device 20 outside of the indentation model 23.

In a final descending step, the instrument tip model 13 is descended onto the indentation model 23 along a descending vector V4 along the base axis Z. Since the gradient of the indentation model 23 is fixed, the descending vector V4, being the shortest of a plurality of descending direction vectors (not shown), from the shifted first collision point C1', the second collision point C2 and the third collision point C3 along the base axis Z onto the indentation model 23 is equally long from all three of those points. Thus, a final first collision point C1'', a final second collision point C2' and a final third collision point C3' can be determined on the indentation model 23, as can be seen in FIG. 10a and FIG. 10b. In this case, the distances from the first collision point C1'', the second collision point C2' and the third collision point C3' to the indentation model 23, respectively, are identical. Thus, three final collision points can be found. In general, the collision point with the shortest distance to the indentation model 23 along the base axis Z determines the final collision point.

Figure 11A:
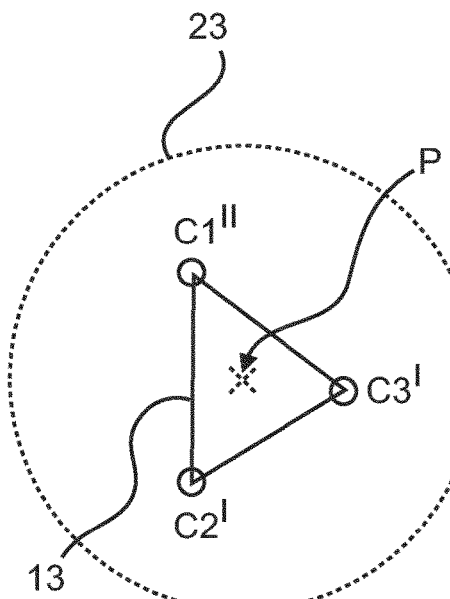
FIG. 11a schematically shows a top view of a final determined position of an instrument tip model in an indentation model.
Figure 11B:
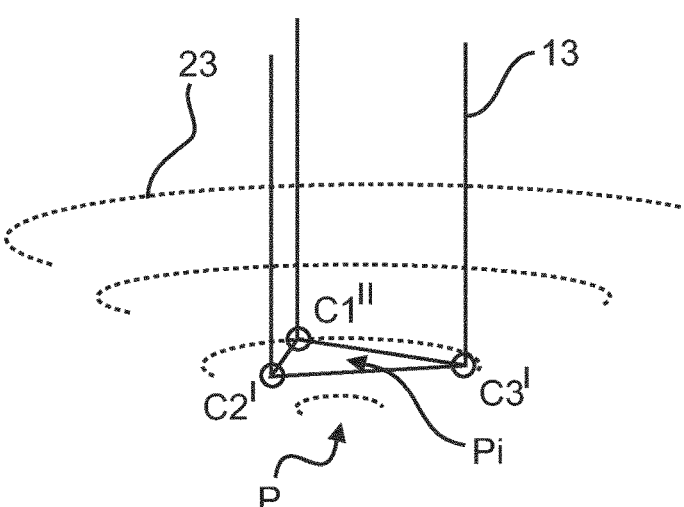
FIG. 11b schematically shows a perspective view of a final determined position of an instrument tip model in an indentation model.

FIG. 11a and FIG. 11b show the instrument tip model 13 and the indentation model 23 after the matching of the instrument tip onto the indentation of the calibration device model 22 is finished.

Thus, the position of the instrument tip model 13 has been determined within the indentation model 23. Using the determined position of the instrument tip model 13 an updated reference point Pi can be determined for usage in a surgical navigation system. The updated reference point Pi relates to the position of a predetermined reference tip point of the instrument tip model 13 in relation to the indentation model 23. The updated reference point Pi consequently is the origin of an instrument model coordinate system, which due to the matching algorithm has a known transformation into a calibration device coordinate system of the calibration device. The matching algorithm determines the position of the instrument tip model 13 in the aforementioned way, however this position is only a snapshot. One calculation based on the matching algorithm therefore relates to one single frame taken by a tracking device. In order to improve the accuracy of the position, the matching algorithm is executed depending on multiple frames. Preferably, the spatial orientation of the instrument tip model 13 in the indentation model 23 is different for each different frame. Further preferably, the instrument tip model 13 is rotated within the indentation model 23 while the different frames of the instrument tip model 13 are taken. From the different determined positions of the instrument tip model 13 based on the different frames, an average position of the instrument tip model 13 can be determined. Thus, the accuracy of the determined position can be further improved.

Figure 12A:
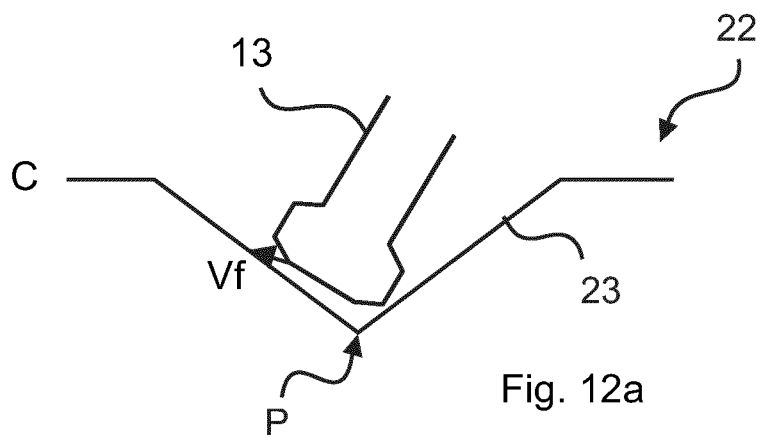
FIG. 12a schematically shows a force shifting step of an instrument tip model onto an indentation model of a calibration device model.

FIG. 12a illustrates an extension of the presented matching algorithm. In real life, the user of the instrument might not use the instrument within the indentation 21 of the calibration device 20 in the most ideal way. If the user holds the instrument in a very acute angle to the surface C of the calibration device 20, the instrument tip 11 might not behave the usual way within the indentation 21. The user generally presses the instrument with some force from the instrument handle to the instrument tip 11. The force will likely cause the instrument tip 11 to be only blocked by an opposing surface of the indentation 21. Therefore, the instrument tip is modelled to ascend in a force shifting step within the indentation 21 by a given threshold along a force vector Vf. Thus, from all force shifting direction vectors (not shown) of different surface points of the instrument tip model 13 towards the indentation model 23 along a common force shifting direction vectors (not shown), the shortest vector is determined to be the force vector Vf, which defines the ascending amount, which the instrument tip model 13 is ascended onto the indentation model 23.

Figure 12B:
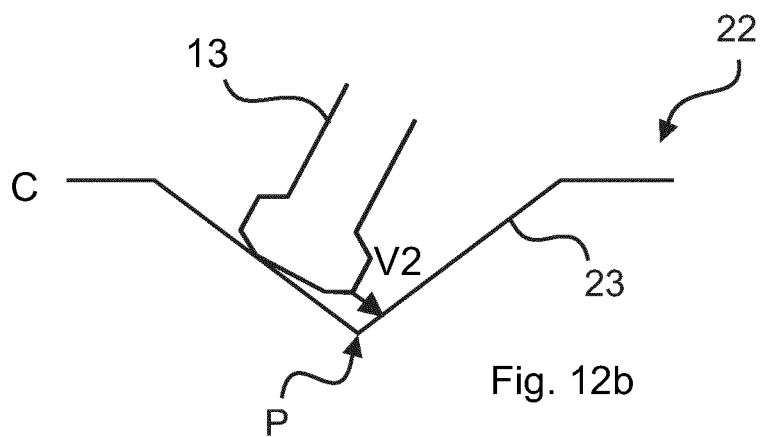
FIG. 12b schematically shows a back shifting step of an instrument tip model onto an indentation model of a calibration device model after a force shifting step.

Afterwards, a back shifting step is executed, which is illustrated in FIG. 12b. The back shifting step basically works like the first descending step. The instrument tip model 13 is shifted onto the indentation model 23 along the gradient of the indentation model 23 towards the reference point P of the indentation model 23. The gradient of the indentation model 23 defines a common first shifting direction vector (not shown). The point, where the instrument tip model 13 collides with the indentation model 23 along a first shifting direction vector (not shown) defines the collision point of the instrument tip model 13 with the indentation model 23. From all first shifting direction vectors (not shown) of different surface points of the instrument tip model 13 towards the indentation model 23 along the common first shifting direction vector (not shown), the shortest vector is determined to be a first shifting vector V2, which defines the shifting amount, which the instrument tip model 13 is shifted onto the indentation model 23.

Figure 13:
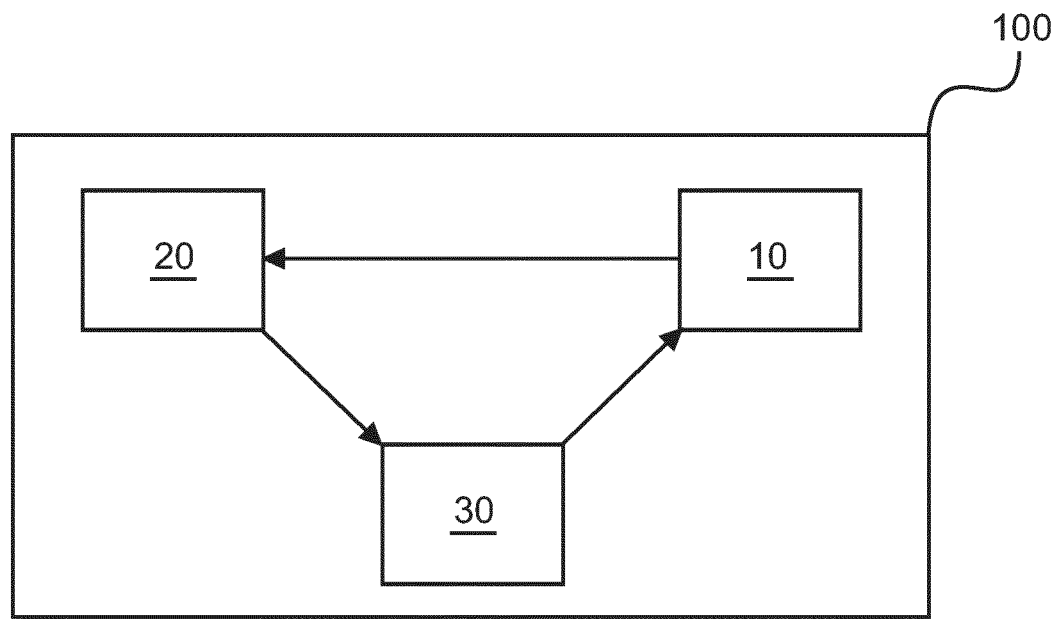
FIG. 13 schematically shows a surgical navigation system.

FIG. 13 schematically shows an instrument calibration system 100 comprising a medical instrument 10 with a tracker and a tracking device 30, configured for tracking the tracker arranged on the medical instrument 10. The instrument calibration system 100 is configured for executing the described method of calibrating the instrument.

For a precise tracking, the instrument 10 has to be calibrated by the calibration device 20, so the tracking device 30 is provided with a calibrated position of the instrument 10. Based on the calibrated position of the instrument 10, relative movements of the instrument 10 can be tracked by the tracking device 30. A surgical navigation system using the calibrated instrument 10 therefore is always aware of the exact position of the instrument 10 relative to the tracking device 30.

The invention claimed is:

1. A computer implemented method of calibrating a medical instrument, the method comprising:
   providing an instrument model comprising an instrument tip model, wherein the instrument tip model is a virtual model of a shape of the medical instrument comprising an instrument tip;
   providing a calibration device model comprising an indentation model, wherein the indentation model is a virtual model of a shape of a calibration device comprising an indentation onto which the instrument tip is introduced for calibration;
   matching the instrument tip model onto the indentation model, thereby determining a position of the instrument tip model within the indentation model; and
   calibrating the medical instrument, thereby using the determined position of the instrument tip model.

2. The method according to claim 1, further comprising:
   tracking the medical instrument by a tracking device, wherein the tracking device comprises a passive tracker arranged on the medical instrument.

3. The method of claim 1, wherein matching the instrument tip model onto the indentation model comprises:
determining an instrument model coordinate system; and
calibrating the medical instrument, thereby using the determined instrument model coordinate system.

4. The method of claim 3, wherein calibrating the medical instrument comprises:
determining an instrument-marker-to-instrument-tip-coordinate-transformation, which describes a transformation between an instrument marker coordinate system and an instrument tip coordinate system, thereby using the determined instrument model coordinate system.

5. The method of claim 4, wherein calibrating the medical instrument comprises:
providing a calibration-device-to-instrument-tip-coordinate-transformation, which describes a transformation between a calibration device coordinate system and the instrument tip coordinate system; and
determining the instrument-marker-to-instrument-tip-coordinate-transformation, thereby using the calibration-device-to-instrument-tip-coordinate-transformation.

6. The method according to claim 1, comprising:
determining an actual spatial orientation of the medical instrument along an axis of the medical instrument; and
using the determined actual spatial orientation during matching the instrument tip model onto the indentation model.

7. The method according to claim 6, wherein determining the actual spatial orientation comprises determining the actual spatial orientation based on a result of tracking the medical instrument.

8. The method according to claim 6, comprising:
determining the actual spatial orientation based on estimating the axis of the medical instrument and/or based on learning from a rotation movement of the instrument tip in the indentation, which is recorded by a tracking device.

9. The method according to claim 1, comprising:
generating a plurality of frames of different positions of the instrument tip in the indentation by using a surgical navigation device;
matching the instrument tip model onto the indentation model for each frame of the plurality of frames and determining a position of the instrument tip model within the indentation model for each frame of the plurality of frames; and
calculating an average position of the instrument tip model based on the determined positions of the instrument tip models of the plurality of frames.

10. The method according to claim 1, wherein matching the instrument tip model onto the indentation model comprises:
calculating, based on the instrument tip model and the indentation model, at least one collision point (between the instrument tip model and the indentation model; and
determining the position of the instrument tip model within the indentation model, thereby using the at least one collision point.

11. The method according to claim 1, comprising:
placing the instrument tip model onto a reference point of the calibration device model;
executing an elevation step, the elevation step comprising elevating the instrument tip model onto the indentation model along a base axis perpendicular to a surface of the calibration device model, thereby determining a first collision point; and
executing at least one first descending step, the at least one first descending step comprising shifting the instrument tip model onto the indentation model along a known gradient of the indentation model from the first collision point towards the reference point of the calibration device model, thereby determining a second collision point and a shifted first collision point.

12. The method according to claim 11, comprising:
determining a third collision point by virtually shifting the instrument tip model onto the indentation model along a horizontal shifting vector, which is a projection of a gradient of the indentation model from a centre point between the shifted first collision point and the second collision point towards the reference point of the calibration device model in a horizontal plane through the centre point;
repositioning the instrument tip model to an average position between the shifted first collision point, the second collision point and the third collision point in the horizontal plane; and
descending the instrument tip model onto the indentation model along the base axis, thereby determining a final collision point.

13. The method according to claim 11, wherein the instrument tip model comprises a mesh of surface points; and comprising:
determining, by an elevation vector, the elevation of the instrument tip model onto the indentation model, wherein the elevation vector is the longest vector between the respective surface points of the instrument tip model and the indentation model along the base axis.

14. The method according to claim 11, wherein the gradient of the indentation model of the calibration device model determines a common shifting direction vector towards the reference point of the calibration device model; and comprising:
determining, by a shifting vector, a shifting amount, wherein the shifting vector is the shortest vector between respective surface points of the instrument tip model and the indentation model along the common shifting direction vector.

15. The method according to claim 11, comprising:
determining a force vector correlating to an estimated force applied onto the medical instrument by a user based on the shape of the indentation; and
executing a force shifting step, the force shifting step comprising shifting the instrument tip model onto the indentation model along the determined force vector.

16. The method according to claim 1, wherein a surface of the instrument model comprises a mesh of surface points, wherein the method comprises:
optimizing the surface of the instrument model by one or more of the following:
reducing the surface of the instrument model to a relevant surface;
mesh optimization; and/or
transforming the surface of the instrument model into a local coordinate system of the indentation model.

17. The method according to claim 1, wherein the shape of the indentation is a cone or a pyramid.

18. An instrument calibration system comprising:
a medical instrument with a tracker; and
a tracking device configured for tracking the tracker arranged on the medical instrument,
wherein the instrument calibration system is configured to:

provide an instrument model comprising an instrument tip model, wherein the instrument tip model is a virtual model of a shape of the medical instrument comprising an instrument tip;

provide a calibration device model comprising an indentation model, wherein the indentation model is a virtual model of a shape of a calibration device comprising an indentation onto which the instrument tip is introduced for calibration;

match the instrument tip model onto the indentation model, thereby determining a position of the instrument tip model within the indentation model; and calibrate the medical instrument, thereby using the determined position of the instrument tip model.

19. A surgical navigation system for computer assisted surgery, the surgical navigation system comprising an instrument calibration system according to claim 18.

20. A non-transitory computer readable storage medium storing a program for calibrating a medical instrument, that when executed on at least one processor of a computer or loaded onto the at least one processor of the computer, causes the computer to:

provide an instrument model comprising an instrument tip model, wherein the instrument tip model is a virtual model of a shape of the medical instrument comprising an instrument tip;

provide a calibration device model comprising an indentation model, wherein the indentation model is a virtual model of a shape of a calibration device comprising an indentation onto which the instrument tip is introduced for calibration;

match the instrument tip model onto the indentation model, thereby determining a position of the instrument tip model within the indentation model; and calibrate the medical instrument, thereby using the determined position of the instrument tip model.

\* \* \* \* \*